(12) United States Patent
Oumi et al.

(10) Patent No.: US 7,238,947 B2
(45) Date of Patent: Jul. 3, 2007

(54) MEDICAL INFORMATION PROCESSOR, IMAGE PHOTOGRAPHING SYSTEM, AND ABSORPTION COEFFICIENT CALIBRATION METHOD

(75) Inventors: Hiroyuki Oumi, Yokohama (JP); Hiroyuki Urushiya, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/217,609

(22) Filed: Sep. 2, 2005

(65) Prior Publication Data

US 2006/0049358 A1    Mar. 9, 2006

(30) Foreign Application Priority Data

Sep. 3, 2004    (JP) ............... 2004-257623

(51) Int. Cl.
*G01T 1/24*    (2006.01)
(52) U.S. Cl. ............................... 250/370.08
(58) Field of Classification Search ........... 250/370.08; 378/4, 7, 14, 19; 382/131, 275
See application file for complete search history.

(56) References Cited

U.S. PATENT DOCUMENTS

| | | | | |
|---|---|---|---|---|
| 4,149,249 A | * | 4/1979 | Pavkovich | .................. 378/14 |
| 5,245,648 A | * | 9/1993 | Kinney et al. | ................. 378/43 |
| 5,293,312 A | * | 3/1994 | Waggener | .................... 378/14 |
| 5,307,254 A | * | 4/1994 | Russello et al. | ............ 362/368 |
| 5,349,951 A | * | 9/1994 | Ito et al. | ..................... 600/310 |
| 5,615,279 A | * | 3/1997 | Yoshioka et al. | ........... 382/131 |
| 5,680,427 A | * | 10/1997 | Dobbs et al. | .................. 378/19 |
| 5,751,243 A | * | 5/1998 | Turpin | ......................... 342/179 |
| 6,845,142 B2 | | 1/2005 | Ohishi | ............................. 378/8 |
| 6,950,494 B2 | * | 9/2005 | Vija et al. | ..................... 378/62 |
| 2003/0031299 A1 | | 2/2003 | Ohishi | ........................ 378/162 |
| 2005/0276371 A1 | | 12/2005 | Urushiya | ........................ 378/4 |
| 2005/0276375 A1 | | 12/2005 | Urushiya | ..................... 378/19 |
| 2006/0029526 A1 | | 2/2006 | Urushiya | ........................ 378/4 |

FOREIGN PATENT DOCUMENTS

JP    3-026241    2/1991
JP    2003-000580    1/2003

\* cited by examiner

*Primary Examiner*—David Porta
*Assistant Examiner*—Marcus Taningco
(74) *Attorney, Agent, or Firm*—Fitzpatrick, Cella, Harper & Scinto

(57) ABSTRACT

Data of arbitrary penetration thickness can be easily obtained in carrying out a beam hardening calibration. A center tomographic image reconstructed parallel to a center line of a projection data of a water phantom and an X-ray tube is read from an image data server. The read center tomographic image is two-dimensionally modeled on a circle. A radius and a center coordinate of the circle on which the image is two-dimensionally modeled are used to re-arrange the X-ray tube, the sensor, and the modeled circle. Points of intersection A and B of the re-arranged circle and a path along which the X-rays reach the sensor from the X-ray tube are determined to obtain a penetration thickness of the water phantom based on the points of intersection A and B. Accordingly, in order to determine an attenuation property when the X-rays are penetrated through a subject, a larger quantity of data of an output value of a sensor with respect to the penetration thickness is gathered with ease.

22 Claims, 31 Drawing Sheets

CIRCULAR CYLINDER
D8

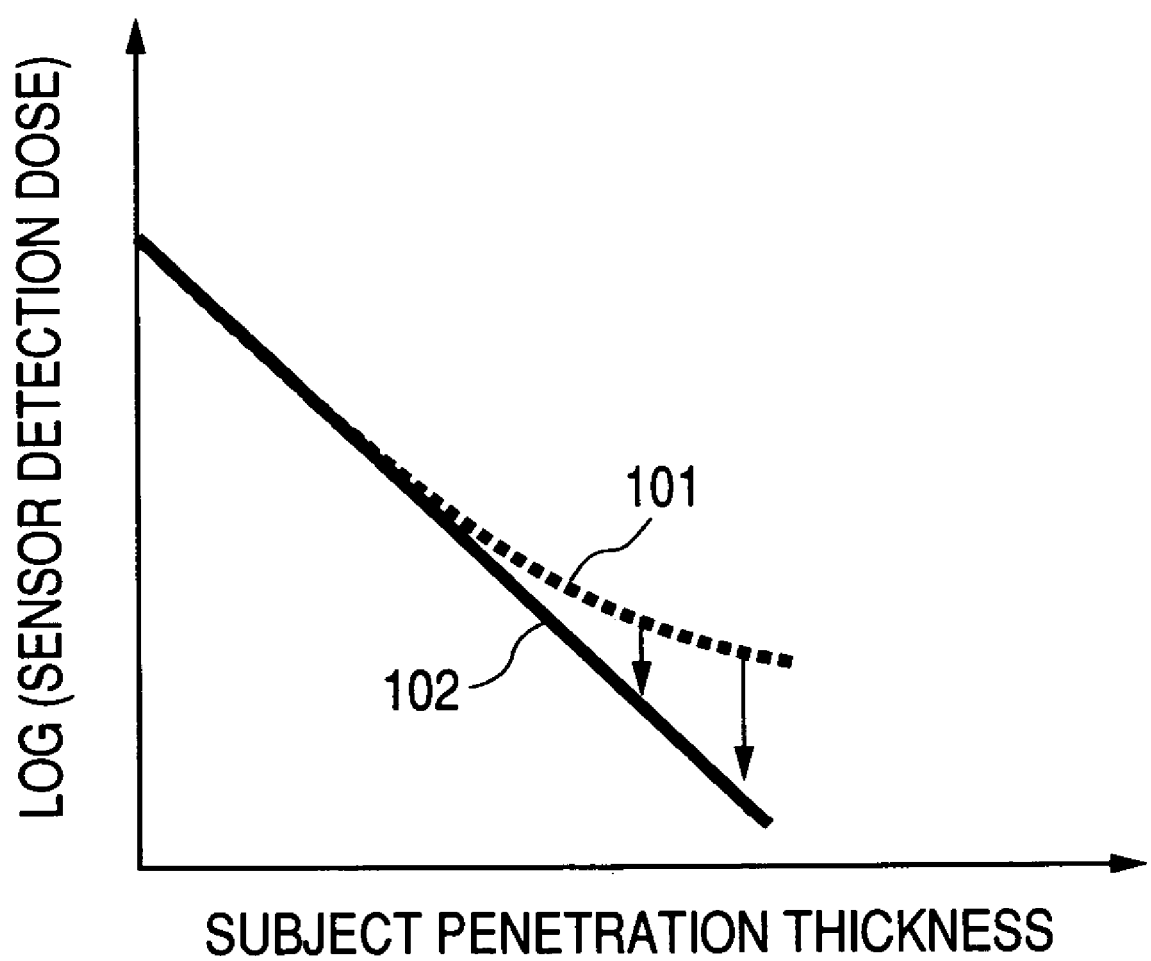

MEDICAL INFORMATION PROCESSOR, IMAGE PHOTOGRAPHING SYSTEM, AND ABSORPTION COEFFICIENT CALIBRATION METHOD

BACKGROUND OF THE INVENTION

1. Field of the Invention

The present invention relates to a medical information processor, an image photographing system, and an absorption coefficient calibration method, and more particularly to an information processor, an image photographing system and an absorption coefficient calibration system which are preferably used in order to carry out a beam hardening calibration.

2. Related Background Art

It is necessary to consider that X-rays emitted from a radiation source of an X-ray CT (Computed Tomography) apparatus are not X-rays of monochromatic energy but X-rays of multi-color energy. It is because when a sensor output value with respect to the X-rays after the penetration of a subject is detected and then a radiation absorption coefficient u of a X-ray penetration section is determined, a change in X-ray spectrum-caused by a penetration thickness of the subject has bad influence on a reconstruction image (tomographic image).

That is, as a photon becomes lower in energy in the X-rays, its attenuation becomes greater, and as the penetration thickness of the subject becomes larger, the X-ray material becomes further stiffened (a high energy component of a spectrum becomes relatively large). Thus, as shown in FIG. 22, a property 102 of the sensor output value that is ideally linearly changed with respect to the penetration thickness indicates a non-linear property 101.

Thus, even if a circular cylinder member 103 made of a uniform material shown in FIG. 23A is used as the subject and then data of a section 104 thereof is gathered to obtain the reconstruction image, the radiation absorption coefficient p becomes low in the center of the section 104 having a large penetration thickness. For this reason, as shown in FIG. 23B, the radiation absorption coefficient p ought to be originally distributed as indicated by a property 105. However, it is distributed as indicated by a property 106, and a tomographic image is consequently configured (such phenomenon is referred to as a beam hardening phenomenon).

Thus, unless the variation in the sensor output with respect to the X-rays after the penetration through the subject is suppressed, or unless the variation is monitored and the variation component and the attenuation property received at the time of the actual subject penetration are taken into consideration to carry out a proper data calibration, an accurate inspection cannot be executed. In this case, a method is usually employed in which the variation in the sensor output is monitored and a predetermined calibration corresponding to the variation in the sensor output with respect to the X-rays after the penetration through the subject and corresponding to the attenuation property received when the X-rays are penetrated through the subject is carried out.

Such method is required to obtain the attenuation property when the X-rays are penetrated through the subject, and the output values for various penetration thicknesses are gathered. Then, when the output values for the various penetration thicknesses are gathered, conventionally, phantoms having various penetration thicknesses are imaged, and output values are determined, as described in (Japanese Patent Application Laid-open No. 2003-000580) and (Japanese Patent Application Laid-open No. H03-026241)

However, in order to determine the attenuation property when the X-rays are penetrated through the subject, many data are required to be gathered. Also, if the phantoms whose penetration thicknesses are different, there is a limit to a data amount to be gathered. Thus, any penetration thickness cannot be selected, and an approximation to the penetration thickness different from the penetration thickness of the imaged phantom becomes very rough. Moreover, measuring the many data takes a longer measurement time corresponding thereto.

In this way, the conventional art has a problem in that at the time of the beam hardening calibration it is very difficult to obtain the data of any penetration thickness.

SUMMARY OF THE INVENTION

The present invention has been made in view of the above problems, and has an object to easily obtain data of arbitrary penetration thickness in carrying out a beam hardening calibration.

An information processor according to the present invention includes: output value reading means for reading an output value of a sensor where a projection data of an object is generated; penetration thickness calculating means for calculating a penetration thickness of a radiation penetrated through the object by using a three-dimensional reconstruction image data in accordance with the projection data of the object; and calibration amount calculating means for calculating a calibration amount to calibrate an absorption coefficient of the radiation by using a correspondence between the output value of the sensor and the penetration thickness of the radiation.

An image photographing system according to the present invention includes: the information processor; an image photographing apparatus for image photographing the object by using the radiation; and a reconstruction processor for generating a three-dimensional reconstruction data of the object, in which the reconstruction processor uses the calibration amount calculated by the object information processor to carry out a beam hardening calibration, and generates the three-dimensional reconstruction data of a subject by reflecting a result obtained through the beam hardening calibration.

An absorption coefficient calibration method according to the present invention includes the steps of: reading an output value of a sensor in which a projection data of an object is generated; calculating a penetration thickness of a radiation penetrated through the object by using a three-dimensional reconstruction image data reconstructed in accordance with a projection data of the object; and calculating a calibration amount by for calibrating an absorption coefficient of the radiation in the object using a correspondence between the output value of the sensor and the penetration thickness of the radiation.

A computer program according to the present invention causes a computer to execute the steps of: reading an output value of a sensor in which a projection data of an object is generated; calculating a penetration thickness of a radiation penetrated through the object by using a three-dimensional reconstruction image data reconstructed in accordance with a projection data of the object; and calculating a calibration amount for calibrating an absorption coefficient of the radiation in the object by using a correspondence between the output value of the sensor and the penetration thickness of the radiation.

BRIEF DESCRIPTION OF THE DRAWINGS

FIG. 22 is a diagram showing a sensor output value with respect to a penetration thickness.

DESCRIPTION OF THE PREFERRED EMBODIMENTS (First Embodiment)

A first embodiment of the present invention will be described below with reference to the drawings.

In this embodiment, among techniques for calibrating a beam hardening phenomenon occurring in X-ray CT systems, an X-ray CT system for determining an attenuation property with respect to a penetration thickness of a subject is exemplified and explained.

Figure 1:
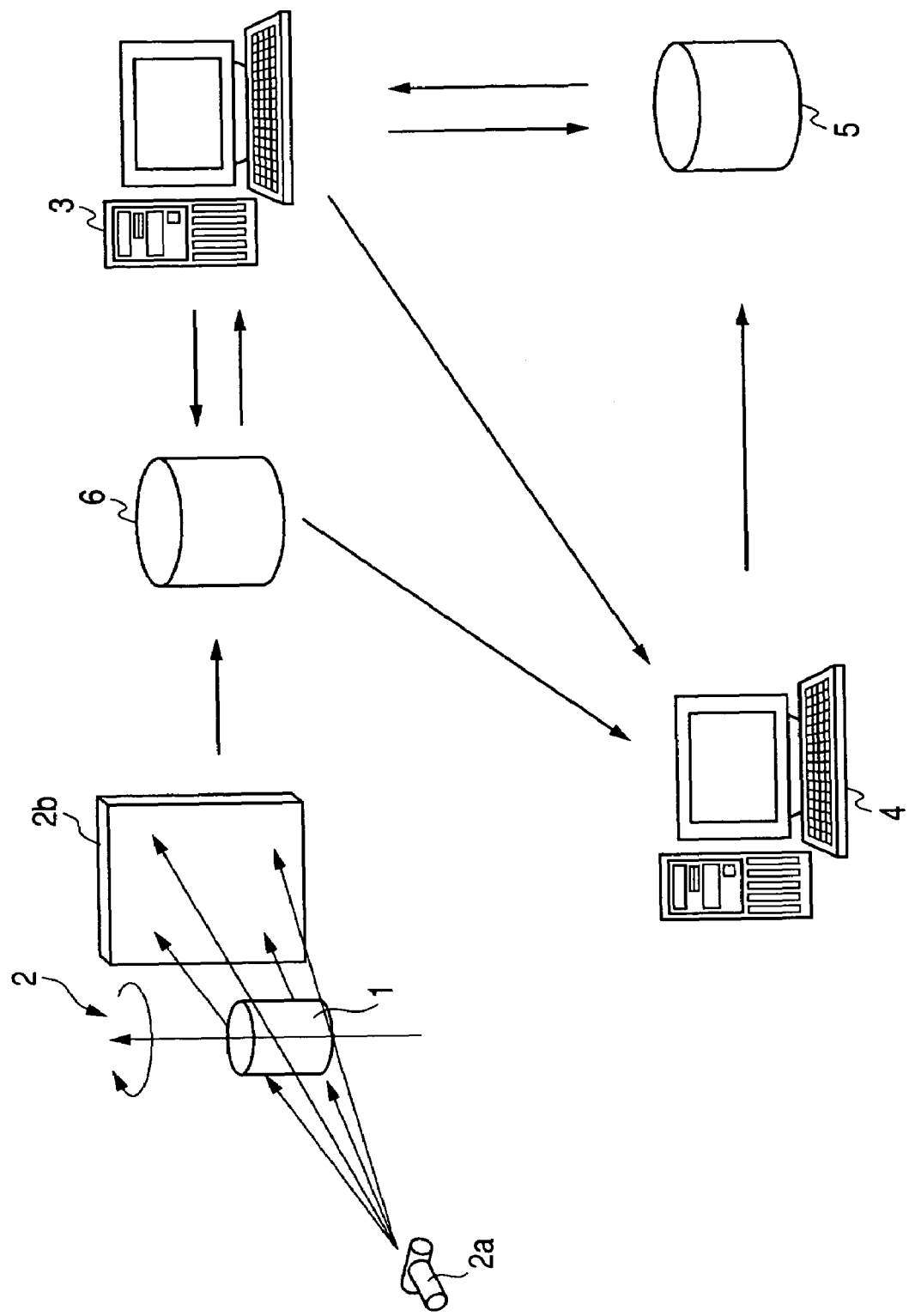
FIG. 1 is a diagram showing a first embodiment of the present invention and showing an example of a configuration of an X-ray CT image photographing system.

FIG. 1 is a diagram showing an example of an X-ray CT image photographing system including a property calculator for determining the attenuation property with respect to the penetration thickness of the subject.

In FIG. 1, the X-ray CT image photographing system is provided with an X-ray CT image photographing device 2 for image photographing a subject 1, a reconstruction processor 3 for generating a reconstruction data from a projection data of the imaged subject 1, a property calculator 4 for determining the attenuation property with respect to the penetration thickness of the subject 1, a calibration data server 5 and an image data server 6.

The reconstruction processor 3, the property calculator 4, the calibration data server 5 and the image data server 6 are connected to each other through a network such as the Internet and the like.

Here, the calibration data server 5 stores a lookup table or calibration function for calibrating the attenuation property, and an ideal radiation absorption coefficient of the subject 1. Also, the image data server 6 stores the projection data where the subject 1 is imaged, and a reconstructed three-dimensional reconstruction data.

In FIG. 1, the numbers of the calibration data servers 5 and the image data servers 6 may be two or more so that they are divided and stored for each kind of stored data. Conversely, the calibration data server 5 and the image data server 6 may be integrated into a single server. The reconstruction processor 3, the property calculator 4, the calibration data server 5 and the image data server 6 are attained by using, for example, a computer having a CPU, a ROM and a RAM, an input device such as a keyboard and a mouse, and a computer system having a monitor.

Here, the flow of-the data between the respective devices disposed in the X-ray CT system in this embodiment is explained with reference to FIGS. 2 and 3.

Figure 2:
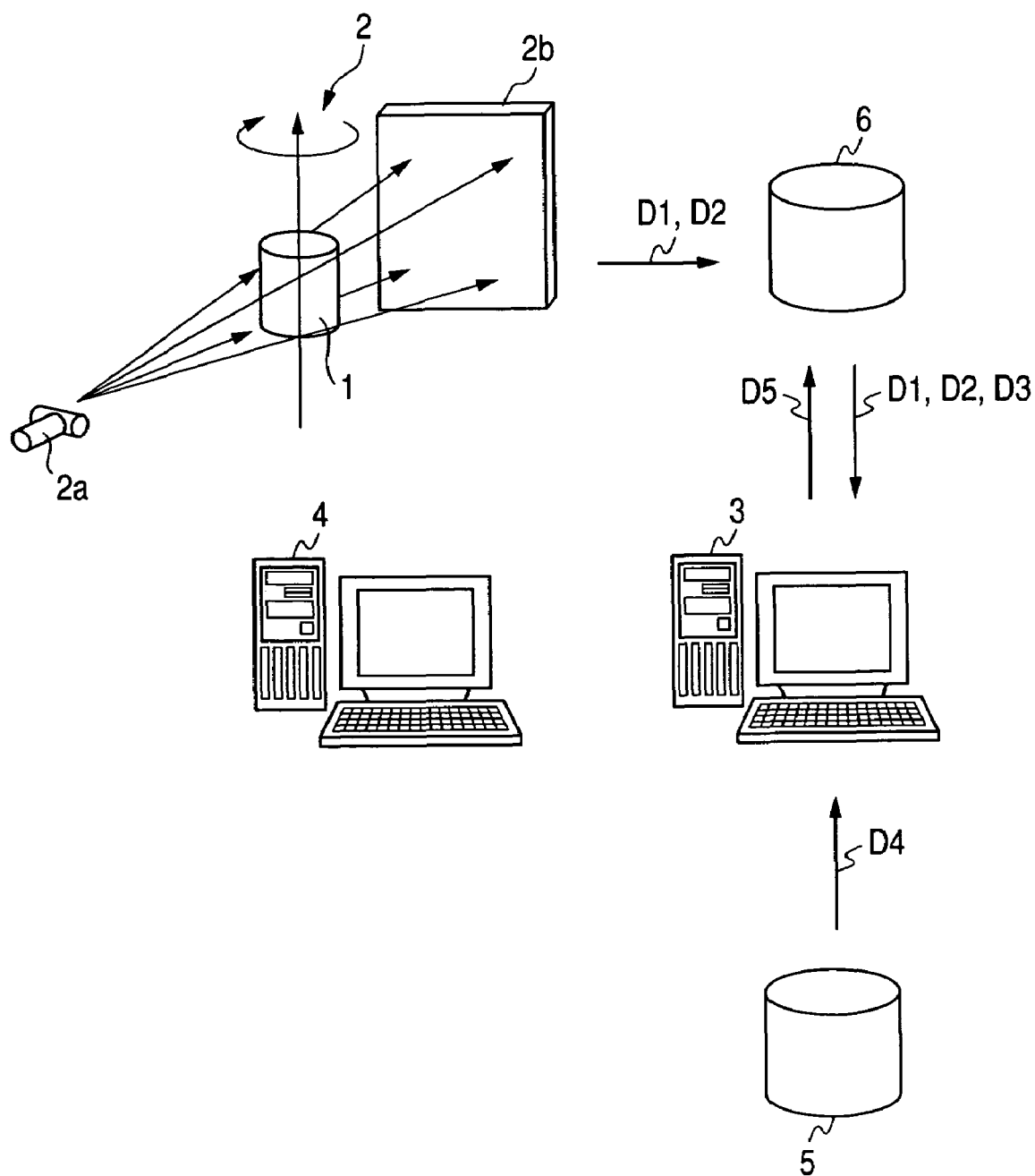
FIG. 2 is a diagram showing the first embodiment of the present invention and showing a flow of data in a case of carrying out a usual image photographing between respective apparatuses disposed in an X-ray CT system.

FIG. 2 shows the flow of the data in a case of carrying out usual image photographing.

In FIG. 2, at first, the X-ray CT image photographing device 2 images the subject 1. A projection data D1 of the imaged subject 1 is transferred to the image data server 6 and stored therein. At this time, an image photographing condition data D2 at the time of the image photographing is simultaneously transferred to the image data server 6 and stored therein.

Next, the reconstruction processor 3 reads the projection data D1 of the subject 1, the image photographing condition data D2 and a water calibration water data D3 from the image data server. 6, in order to reconstruct the three-dimensional reconstruction data. Here, the water calibration water data D3 is the absorption coefficient of water. In this way, if the water calibration water data D3 is inputted to the reconstruction processor 3, the ideal absorption coefficient of the water obtained by the property calculator 4 can be used, obtaining a value more suitable for the image photographing condition, such as a property of the system, than a case of using a physical constant. Thus, the precision of a CT value can be made higher.

Next, the reconstruction processor 3 reads a data (a data for the beam hardening calibration) D4 for calibrating the beam hardening phenomenon from the calibration data server 5.

Then, the reconstruction processor 3 determines the three-dimensional reconstruction data D5 of the subject 1. The three-dimensional reconstruction data D5 is transferred to the image data server 6 and stored therein.

When the process for determining the reconstruction data is executed, the reconstruction of a discrete reconstruction area is executed. Specific example is explained. At first, a tube 2a disposed in the X-ray CT image photographing device 2 emits the X-rays to the subject 1 from the tube 2a, while rotating the subject 1, so as to relatively rotate around the subject 1. Consequently, a sensor 2b disposed oppositely to the tube 2a through the subject 1 receives the X-rays penetrated through the subject 1 and generates the projection data D1 from a plurality of directions, in accordance with the received X-rays. Then, a convolution filter (calibration filter) is used to perform convolution on the obtained projection data D1 from the plurality of directions, and performs inverse projection calculation (inverse projection process) for conversely projecting the projection data D1, on such convolution result, and then generates the three-dimensional reconstruction data D5.

Figure 3:
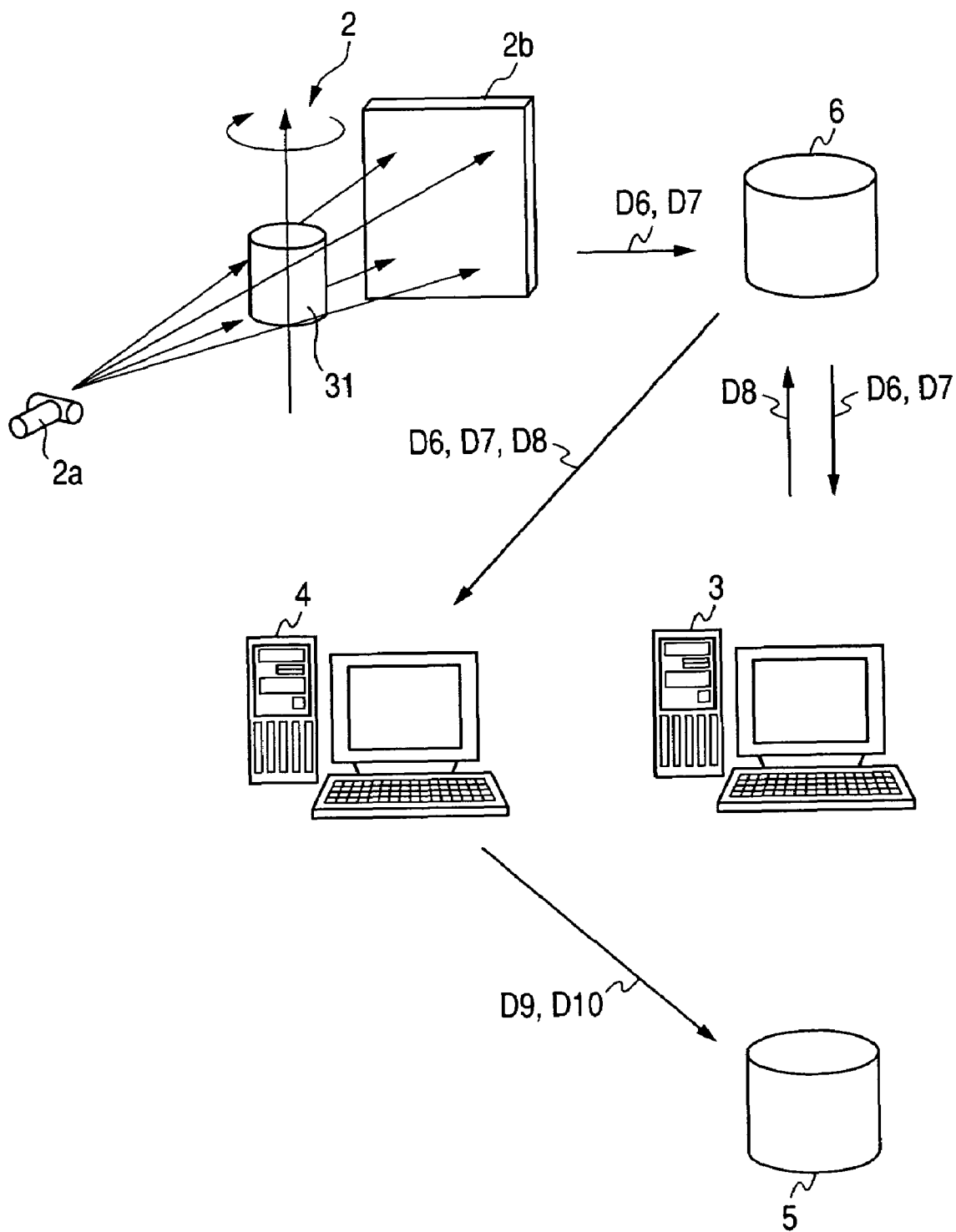
FIG. 3 is a diagram showing the first embodiment of the present invention and showing a flow of data in a case of determining an attenuation property between the respective apparatuses disposed in the X-ray CT system.

FIG. 3 shows the flow of the data when the attenuation property is determined.

In FIG. 3, at first, the X-ray CT image photographing device 2 images a water phantom 31 as a regular material. An imaged projection data D6 is transferred to the image data server 6 and stored therein. At this time, an image photographing condition data D7 at the time of the image photographing is simultaneously transferred to the image data server 6 and stored therein. Here, the reason why the water is selected as the regular material is that about 90% of a human body is constituted by the water. Thus, the attenuation property suitable for the penetration thickness of the water can be used for the calibration of the attenuation property when the human is imaged, namely, the beam hardening calibration.

Next, in order to reconstruct the three-dimensional reconstruction data of the water phantom 31, the reconstruction processor 3 reads the projection data D6 of the water phantom 31 and the image photographing condition data D7 from the image data server 6.

A three-dimensional reconstruction data D8 of the water phantom 31 reconstructed by the reconstruction processor 3 is transferred to the image data server 6 and stored therein. Next, the property calculator 4 reads the three-dimensional reconstruction data D8 of the water phantom 31, the projection data D6 of the water phantom 31 and the image photographing condition data D7 from the image data server 6, in order to obtain the attenuation property with respect to the penetration thickness of the water.

Then, the property calculator 4 calculates the attenuation property with respect to the penetration thickness of the water, considers this attenuation property with respect to the penetration thickness of the water, and transfers a data 9 indicating a calibration amount corresponding to a variation in an X-ray output as a lookup table (a calibration lookup table for an absorption coefficient calibration) to the calibration data server 5. At this time, instead of the data D9 indicating the calibration amount corresponding to the variation in the X-ray output, a calibration function corresponding to the variation in the X-ray output may be transferred to the calibration data server 5.

Also, the property calculator 4 uses the attenuation property with respect to the penetration thickness of the water, and calculates the absorption coefficient of the water and similarly transfers a data D10 indicating the calculated water absorption coefficient to the calibration data server 5. The above lookup table, or the calibration function D9 and the data D10 indicating the water absorption coefficient become the beam hardening calibration data 4 as mentioned above.

The detail of the process executed in the property calculator 4 will be described below.

Figure 4:
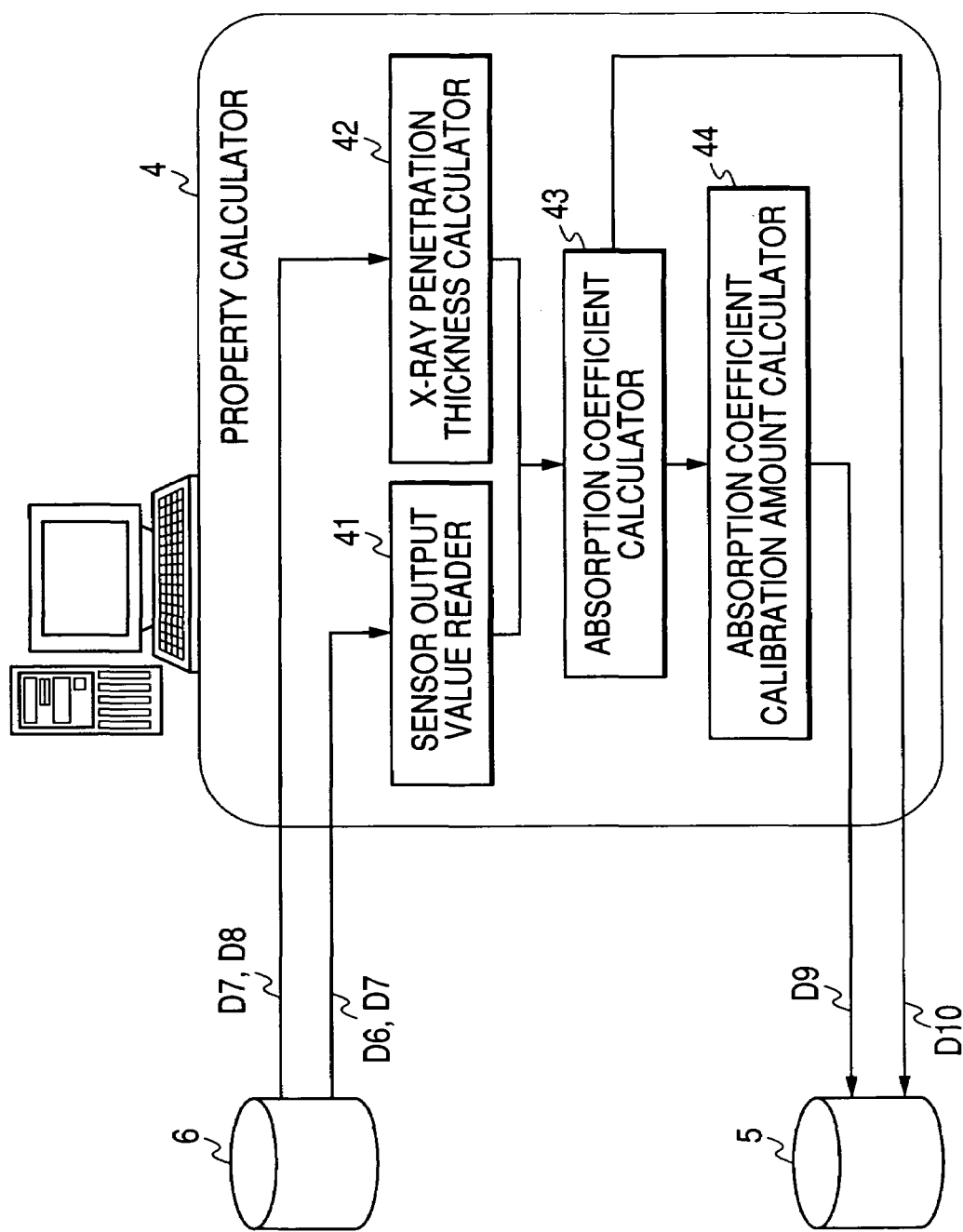
FIG. 4 is a diagram showing the first embodiment of the present invention and showing an example of a function configuration of a property calculator.

FIG. 4 is a diagram showing an example of a function configuration of the property calculator 4. Here, a case of three-dimensionally modeling the water phantom 31 on a circular cylinder is exemplified and explained. The following processes executed by the property calculator 4 are attained, for example, when a CPU of the computer system that is the property calculator 4 executes an application program.

Figure 5:
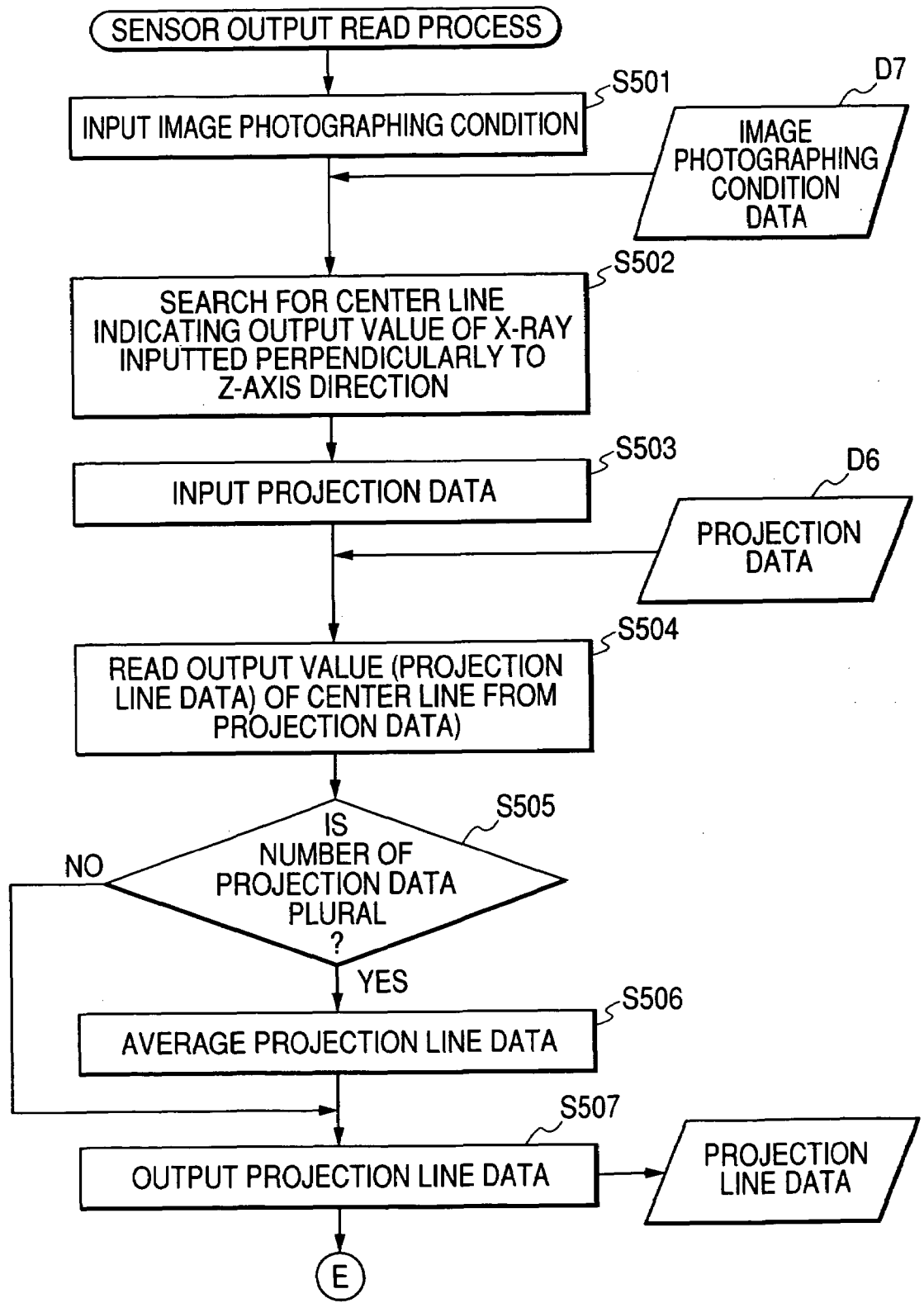
FIG. 5 is a flow chart showing the first embodiment of the present invention and explaining an example of a sensor output read process.

At first, a sensor output value reader 41 reads the projection data D6 of the water phantom 31 and the image photographing condition data D7 when the water phantom 31 is imaged, from the image data server 6 (sensor output read process). Here, an example of a sensor output read process executed by the sensor output value reader 41 is explained by using a flow chart of FIG. 5.

Figure 6A:
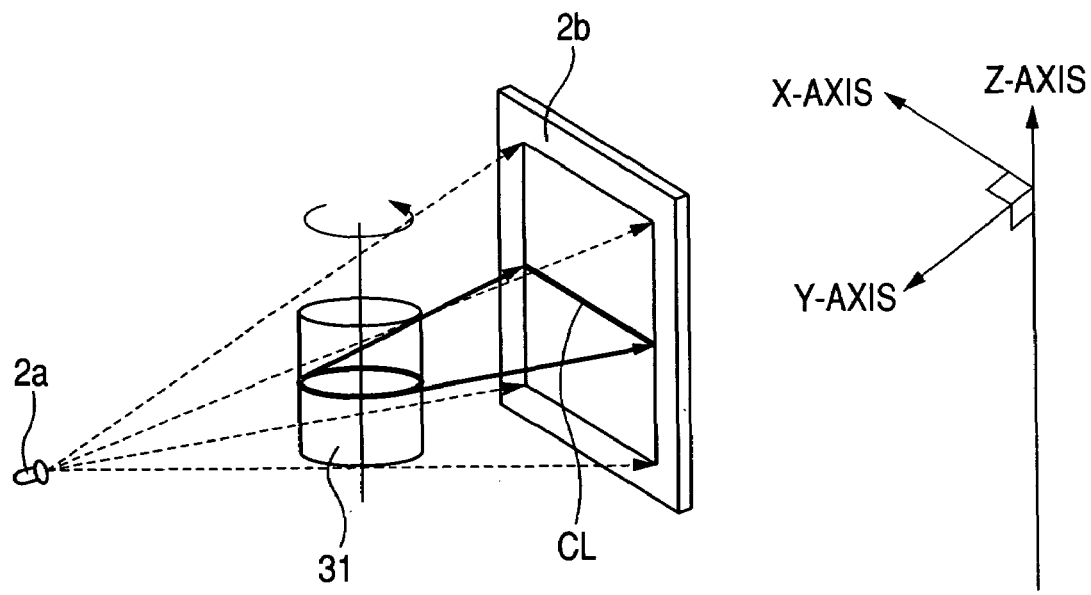
FIGS. 6A and 6B are diagrams showing the first embodiment of the present invention and showing an example of a sensor line inputted to a sensor disposed in the X-ray CT image photographing system.
Figure 6B:
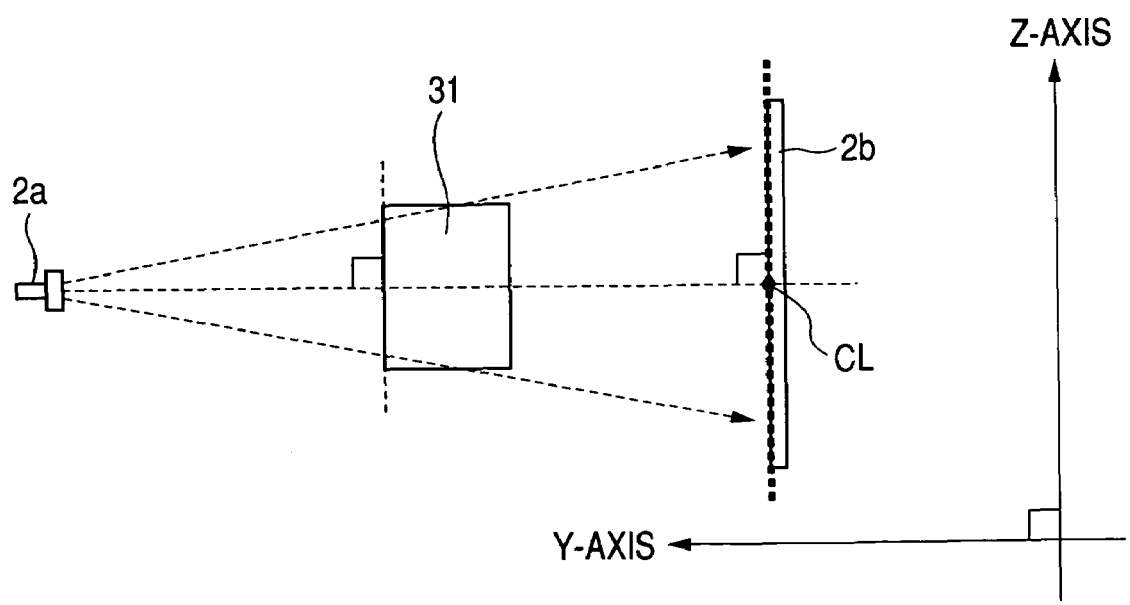

The image photographing condition data D7 when the water phantom 31 is imaged is inputted (Step S501). Then, as shown in FIG. 6A, which number of the sensor line from the top end in a Z-axis direction where the X-rays emitted from the tube 2a disposed in the X-ray CT image photographing device 2 are inputted vertically to the Z-axis direction of the sensor 2b disposed in the X-ray CT image photographing device 2 is determined in accordance with the image photographing condition data D7 (Step S502). Then, a center line CL is determined from this sensor line. FIG. 6B is a diagram when FIG. 6A is viewed from an X-axis direction.

Next, the projection data D6 when the water phantom 31 is imaged is inputted (Step S503). At this time, the number of the inputs of the projection data D6 is arbitrary.

Next, the data of the center line CL is read from the input projection data D6 (Step S504). This data is defined as a projection line data. When the number of the projections is two or more, there are plural pieces of projection line data. Then, the projection line data of the same position are averaged, and the averaged projection line data is again defined as the projection line data obtained from the projection data D6 when the water phantom 31 is imaged (Yes of Step S505, Step S506). The thus-obtained projection line data is outputted as the output of the sensor output read process to an absorption coefficient calculator 43 (Step S507).

Figure 7:
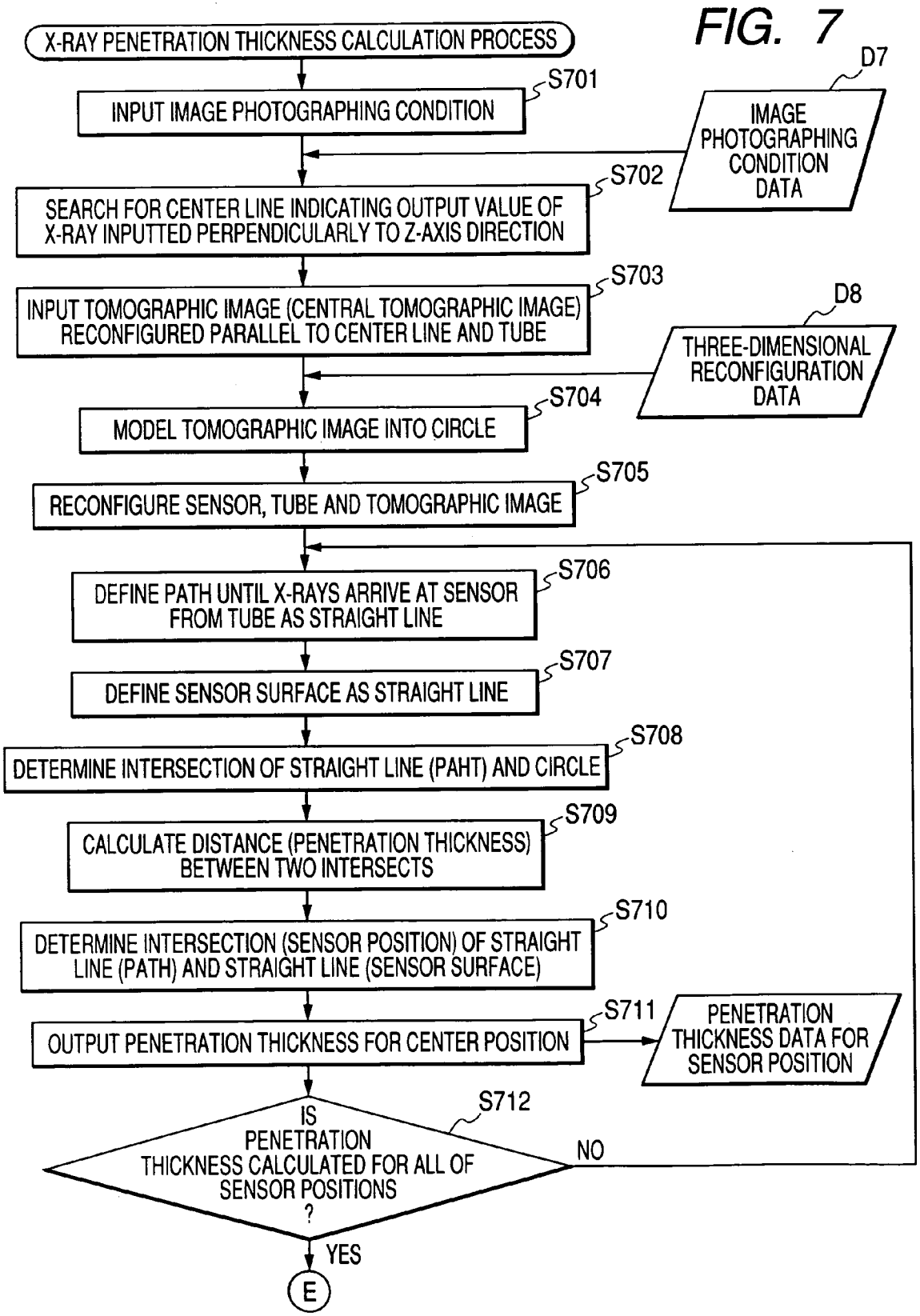
FIG. 7 is a flow chart showing the first embodiment of the present invention and explaining an X-ray penetration thickness calculation process.

Referring again to FIG. 4, when the sensor output read process as mentioned above has been completed, an X-ray penetration thickness calculator 42 reads the three-dimensional reconstruction data D8 of the water phantom 31 and the image photographing condition data D7 when the water phantom 31 is imaged, from the image data server 6 and executes an X-ray penetration thickness calculation process for calculating the penetration thickness that indicates the thickness where the X-rays are penetrated through the water phantom 31. Here, an example of the X-ray penetration thickness calculation process executed by the X-ray penetration thickness calculator 42 is explained using a flow chart of FIG. 7.

Figure 8A:
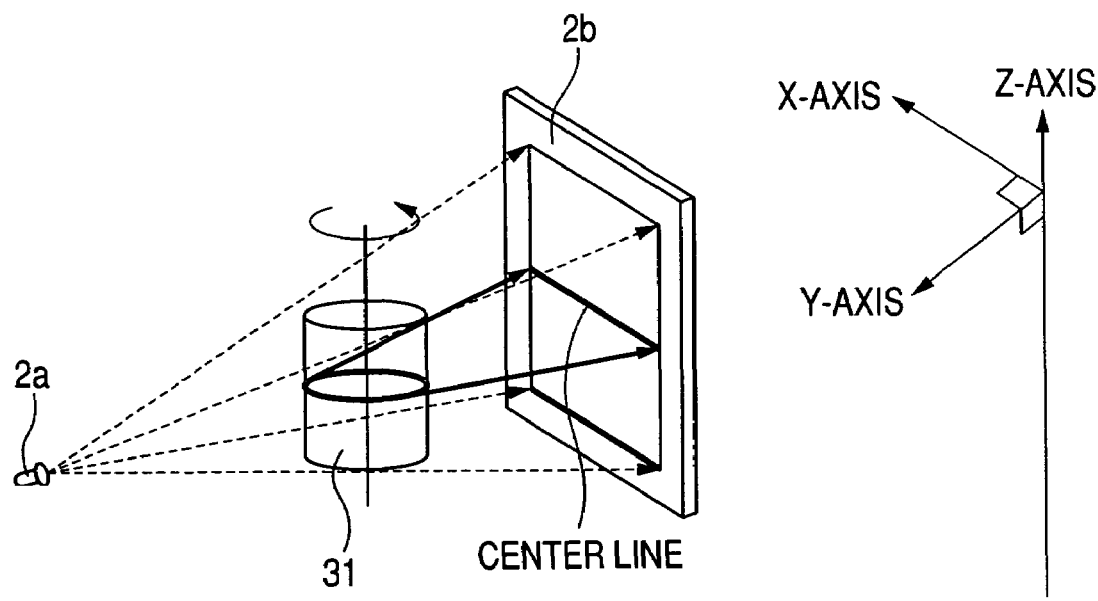
FIGS. 8A, 8B and 8C are diagrams showing the first embodiment of the present invention and showing an example of a center tomographic image.
Figure 8B:
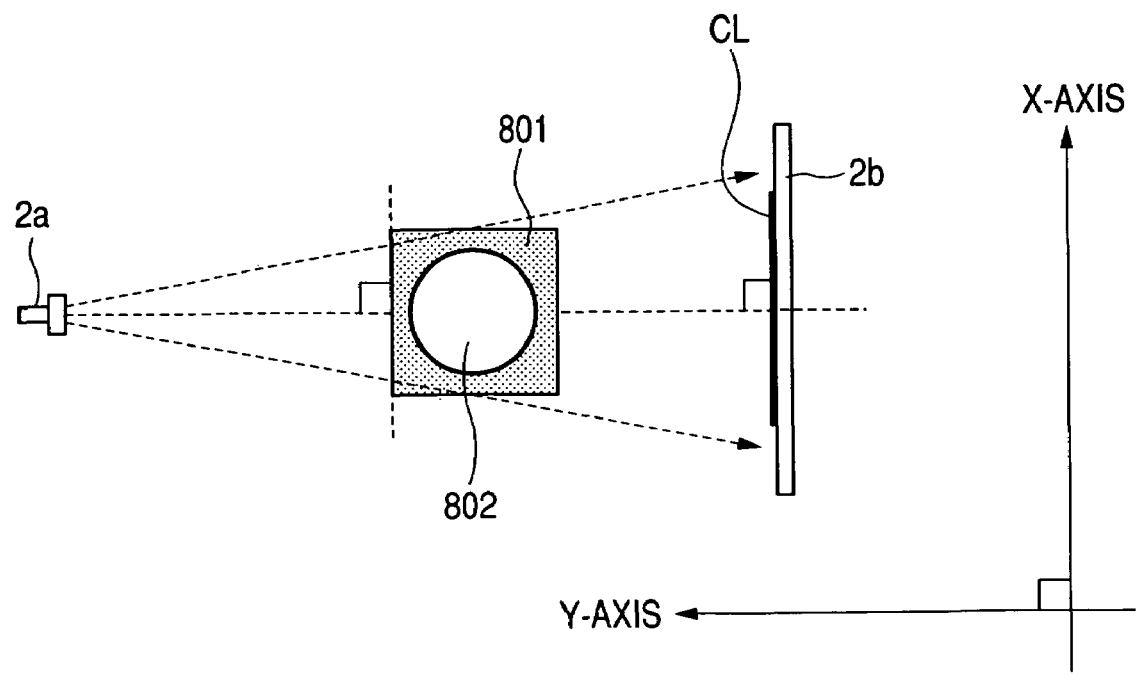
Figure 8C:
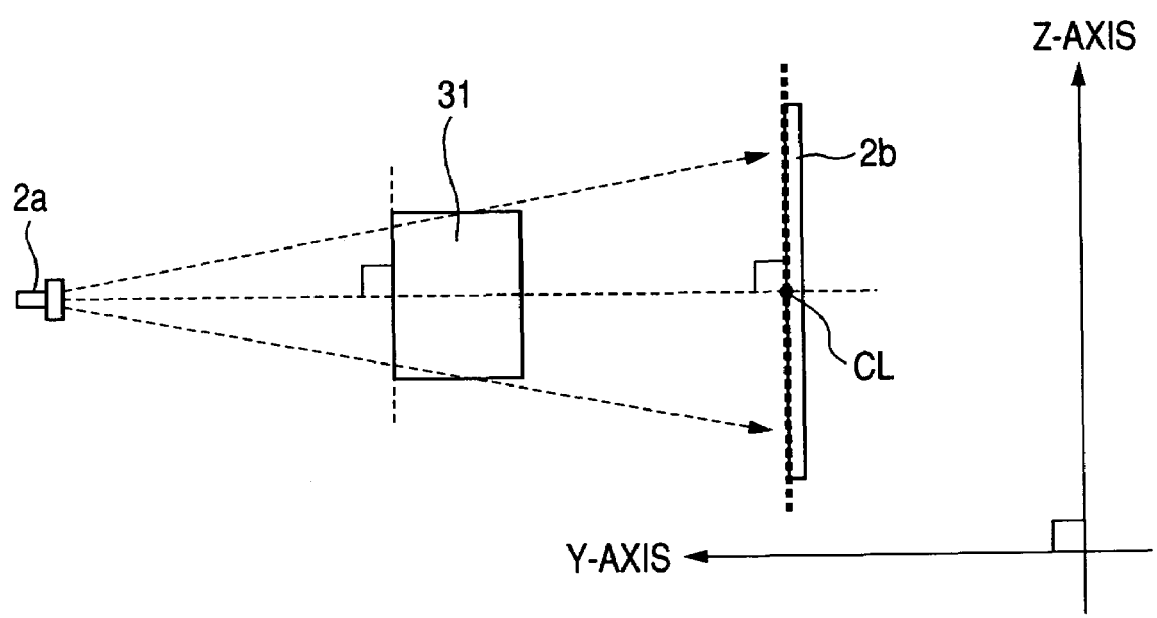

At first, the image photographing condition data D7 when the water phantom 31 is imaged is inputted (Step S701). Then, as shown in FIG. 8A, which number of the sensor line from the top end in the Z-axis direction where the X-rays emitted from the tube 2a are inputted vertically to the Z-axis direction of the sensor 2b is determined in accordance with the image photographing condition data D7, and the center line CL is determined (Step S702). FIG. 8C is a diagram when FIG. 8A is viewed from the X-axis direction.

Next, by inputting the three-dimensional reconstruction data D8 located in the image data server 6, a tomographic image that is reconstructed parallel to the center line CL and the tube 2a is obtained (Step S703). The tomographic image is defined as a center tomographic image 801. The center tomographic image 801 at this time has a relation as shown in FIGS. 8A and 8B. FIG. 8B is the diagram when FIG. 8A is viewed from a Z-axis direction. As shown in FIGS. 8B and 8C, the center tomographic image 801, the tube 2a and the center line CL are located on the same plane and vertical to the Z-axis direction of the sensor 2b.

Next, the center tomographic image 801 is modeled on a circle (Step S704). The reason is as follows. That is, the center tomographic image 801 can be considered such that, since the tube 2a and the center line CL are located on the same plane and vertical to the Z-axis direction of the sensor 2b, the circular cylinder (here, the water phantom 31) is cut on a plane parallel to a bottom plane. If two-dimensional modeling is tried by using an image (a tomographic image that is not vertical to the Z-axis direction of the sensor 2b) except the center tomographic image without using the center tomographic image 801, the circular cylinder (here, the water phantom 31) is assumedly cut on a plane which is not parallel to the bottom plane. Thus, the tomographic image is two-dimensionally modeled on an ellipse.

Figure 9:
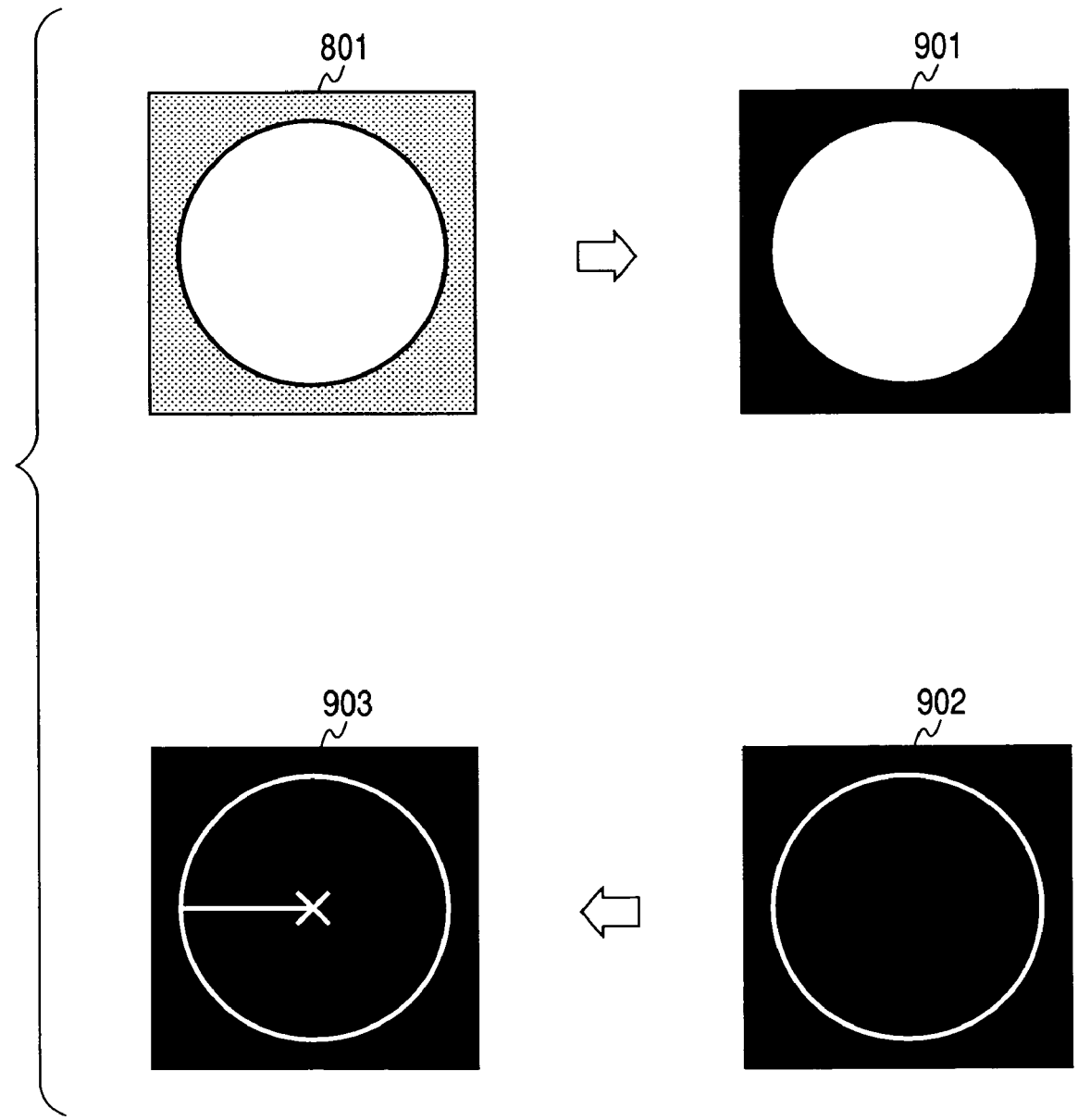
FIG. 9 is a diagram showing the first embodiment of the present invention and showing an example of a manner of modeling a section image of a water phantom in the center tomographic image.

FIG. 9 shows an example of a manner of modeling a tomographic image 802 of the water phantom 31 in the center tomographic image 801 shown in FIG. 8B.

At first, when a binary process is performed on the center tomographic image 801, a binary image 901 of the center tomographic image 801 is obtained. Next, when an edge extraction process is performed on the binary image 901, an edge image 902 of the tomographic image 802 of the water phantom 31 is obtained.

Then, a plurality of test circles whose radiuses and central positions are changed are set. Respective error amounts between the plurality of test circles and the edge image 902 of the tomographic image 802 of the water phantom 31 are then calculated to determine the test circle having the smallest error amount as the circle where the tomographic image 802 of the water phantom 31 in the center tomographic image 801, and a modeling image 903 is obtained. Here, if the modeling is performed on the ellipse, a center, a long axis and a short axis are determined instead of the radius and center.

Figure 10A:
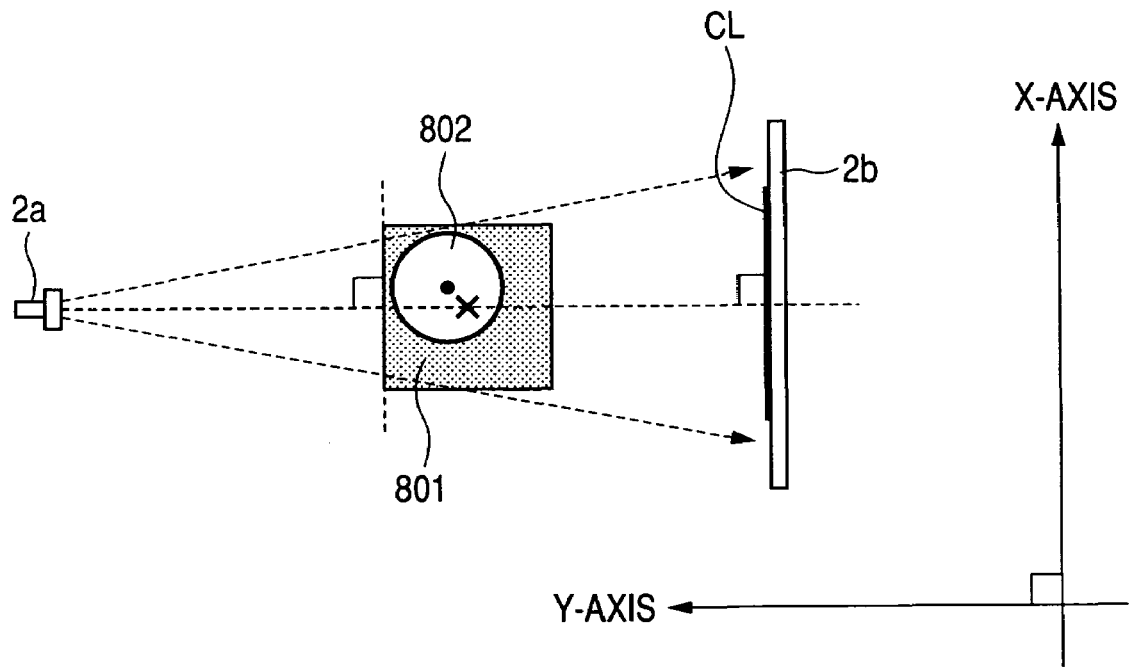
FIGS. 10A and 10B are diagrams showing the first embodiment of the present invention and showing an example of an arrangement between a tube, the sensor, and the center tomographic image before and after re-arrangement.
Figure 10B:
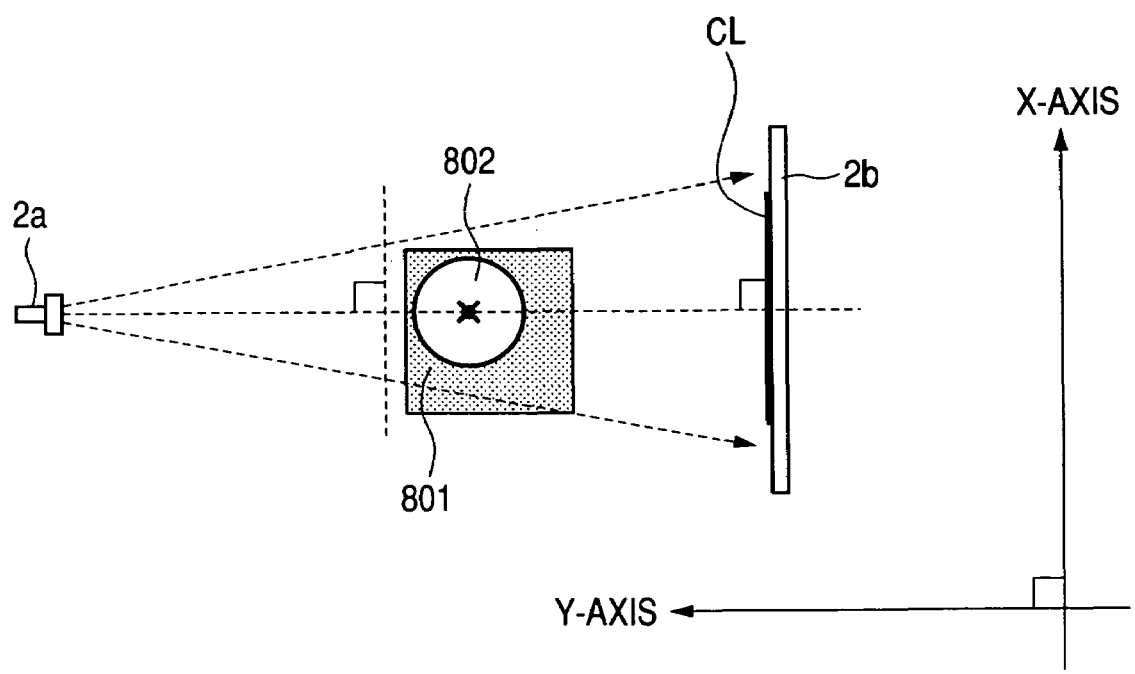

Referring again to FIG. 7, the radius and center coordinate of the circle where the tomographic image 802 of the water phantom 31 in the center tomographic image 801 is used to re-arrange the tube 2a, the sensor 2b and the center tomographic image 801 (Step S705). FIG. 10A shows arrangement of the tube 2a, the sensor 2b and the center tomographic image 801 before the re-arrangement, and FIG. 10B shows arrangement of the tube 2a, the sensor 2b and the center tomographic image 801 after the re-arrangement.

Before the re-arrangement, the center of the center tomographic image 801 is assumed to be the rotation center of the water phantom. Thus, as shown in FIG. 10A, the center of the center tomographic image 801 is set at a position away from the sensor 2b, by a distance to the rotation center of the subject from the sensor 2b included in the image photographing condition data D7, on a straight line through which the tube 2a and the sensor 2b are vertically connected. However, as shown in FIG. 10A, there may be a case where the center of the center tomographic image 801 and the center of the tomographic image 802 of the water phantom 31 are not coincident. Since a process for calibrating a displacement of a rotation axis around which the water phantom 31 is rotated at the time of the reconstruction and the like is executed, there may be a case where the center of the center tomographic image 801 is not coincident with the center of the tomographic image 802 of the water phantom 31. Thus, as shown in FIG. 10B, the re-arrangement is executed such that the center of the tomographic image 802 of the water phantom 31 is located at the position away from the sensor 2b, by the distance to the rotation center of the subject from the sensor 2b included in the image photographing condition data D7, on the straight line through which the tube 2a and the sensor 2b are vertically connected.

Figure 11:
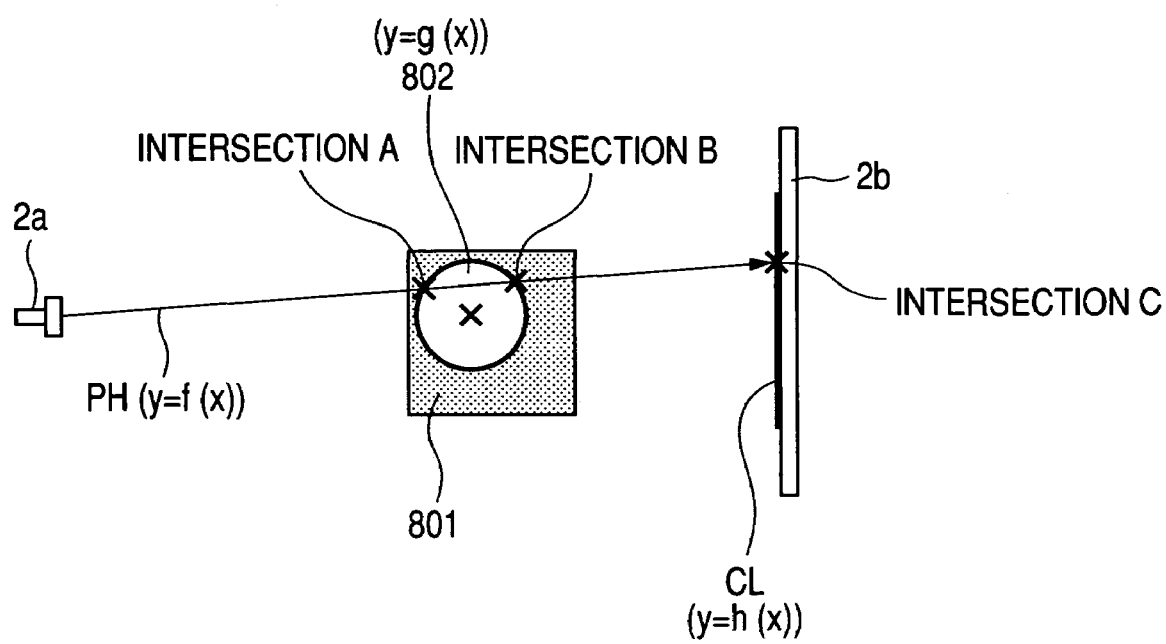
FIG. 11 is a diagram showing the first embodiment of the present invention and showing an example of a point of intersection of a straight line indicating a path along which X-rays reach the sensor from the tube and a circle on which a section image of the water phantom in the center tomographic image is modeled.

Then, as shown in FIG. 11, a path ($y=f(x)$) when the X-rays arrive at the sensor 2b from the tube 2a is determined as a plane straight line PH where the tube 2a, the sensor 2b and the center tomographic image 801 exist (Step S706).

Moreover, the center line is also determined as a plane straight line CL (y=h(x)) where the tube 2a, the sensor 2b and the center tomographic image 801 exist (Step S707). If it is further accurately represented when the sensor 2b is represented by a curved line instead of the straight line, the curved line may be used.

Then, the intersections A, B of: the straight line PH (y=f(x)) indicating the path when the X-rays arrive at the sensor from the tube; and the circle where the tomographic image 802 of the water phantom 31 in the center tomographic image 801 is modeled are determined by solving a quadratic equation. Then, a distance between the intersection A and the intersection B is determined, thereby calculating the penetration thickness (Step S709). Moreover, the intersection C of: the straight line PH (y=f(x)) indicating the path when the X-rays arrive-at the sensor 2b from the tube 2a; and the straight line CL (y=h(x)) indicating the center line is determined by solving a linear equation or quadratic equation (Step S710). This intersection C becomes the position where the X-rays penetrated through the penetration thickness determined by the distance between the intersection A and the intersection B arrive at the sensor 2b, and this correspondence is outputted as the penetration thickness with respect to the position of the sensor 2b, to the absorption coefficient calculator 43 (Step S711).

The processes of the steps S706 to S711 as mentioned above are performed on all of the positions of the sensors 2b on the projection line data. However, the processes are not always required to be performed on all of the positions of the sensors 2b on the projection line data. However, as the number of the correspondences between the penetration thicknesses with respect to the positions of the sensors 2b is smaller, the precision of the finally-determined attenuation property when the X-rays are penetrated through the water is further reduced. Thus, for as many line positions as possible (preferably, all of the line positions), it is preferred to obtain the correspondences between the penetration thicknesses with respect to the positions of the sensors 2b.

Figure 12:
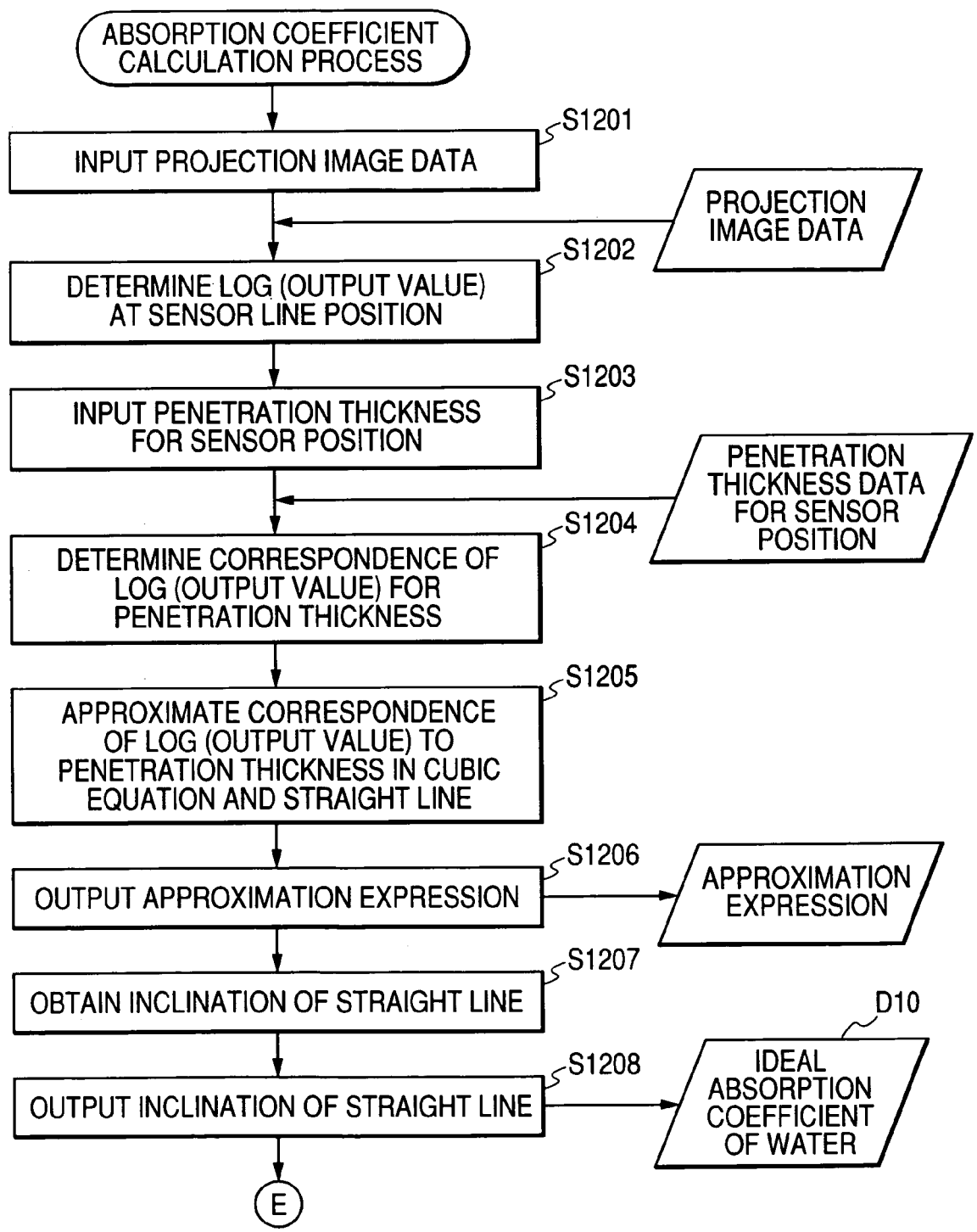
FIG. 12 is a flow chart showing the first embodiment of the present invention and explaining an example of an absorption coefficient calculation process.

Referring back to FIG. 4, the absorption coefficient calculator 43 receives: the projection line data obtained from the result of the sensor output read process in the sensor output value reader 41; and the correspondence between the penetration thickness and the position of the sensor 2b, which is obtained from the result of the X-ray penetration thickness calculation process in the X-ray penetration thickness calculator 42, and carries out the absorption coefficient calculation process for calculating the absorption coefficient of the water. Here, an example of the absorption coefficient calculation process executed by the absorption coefficient calculator 43 is explained using a flow chart of FIG. 12.

At first, the projection line data is inputted (Step S1201). Then, a logarithm is taken of the input projection line data (Step S1202). Consequently, a LOG (output value) at the sensor line position can be determined from the input projection line data. Next, the correspondence of the penetration thickness with respect to the position of the sensor 2b is inputted (Step S1203). The LOG (output value) with respect to the penetration thickness is determined from: the LOG (output value) at the sensor line position that is the result of the step S1202; and the correspondence of the penetration thickness to the position of the sensor 2b. *Consequently, the output value with respect to the penetration thickness is obtained in the logarithm (Step S1204).*

Figure 13A:
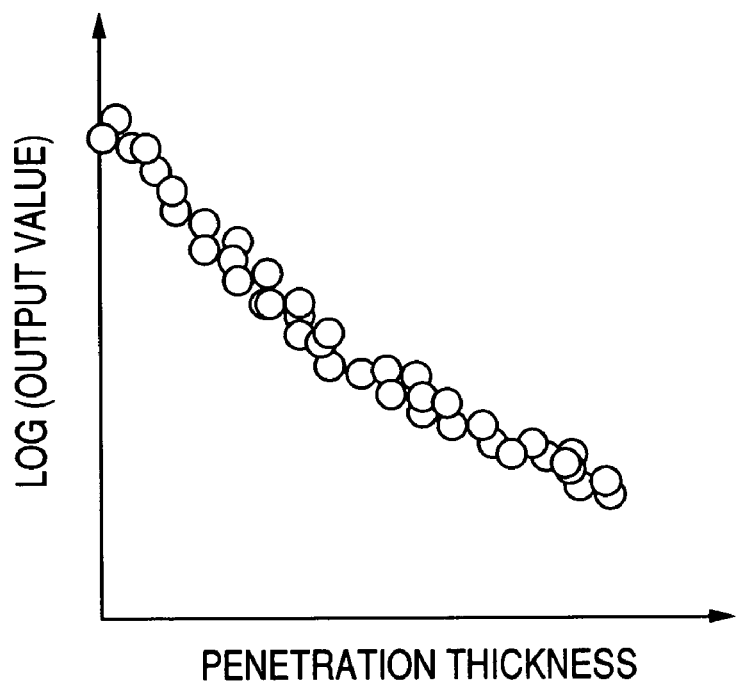
FIG. 13A is a diagram showing the first embodiment of the present invention and showing an example of a relation between an output value and a penetration thickness.
Figure 13B:
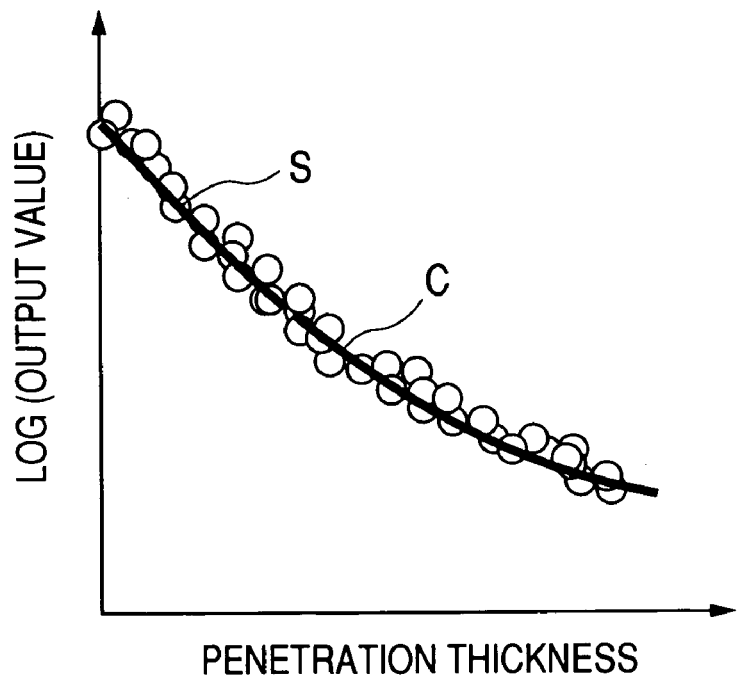
FIG. 13B is a diagram showing the first embodiment of the present invention and showing an approximation expression indicating the relation between the output value and the penetration thickness.

Then, the relation of the output value (LOG (output value)) to the penetration thickness is represented by an approximation expression (Step S1205). Here, the relation of the output value (LOG (output value)) to the penetration thickness is as shown in FIG. 13A. Thus, as shown in FIG. 13B, the approximation is executed so as to carry out the division so that the thin portion of the penetration thickness is represented by a straight line S (a linear equation) and the thick portion of the penetration thickness is represented by a curved line (a cubic equation) However, depending on the image photographing condition, there may be a better case where the approximation is executed by carrying out the division so that the thin portion of the penetration thickness is represented by a curved line (a cubic equation) and the thick portion of the penetration thickness is represented by a straight line (a linear equation). Thus, at that time, it is allowable to employ a method where the approximation is executed by carrying out the division so that the thin portion of the penetration thickness is represented by the curved line (cubic equation) and the thick portion of the penetration thickness is represented by the straight line (linear equation).

Also, as for the boundary between the curved line (cubic equation) and the straight line (linear equation), the optimal place where the error of the approximation becomes small ought to be selected for each data. Since the obtained approximation expression is used by a next process, it is outputted to an absorption coefficient calibration amount calculator 44 (Step S1206).

Next, the inclination of the approximated straight line is determined (Step S1207). The fact where the output value (LOG (output value)) with respect to the penetration thickness is linear indicates that the input X-rays are the monochromatic X-rays. Thus, the fact of this approximated straight line is the ideal relation, and this inclination becomes the absorption coefficient of the water under this image photographing condition. This is referred to as the ideal absorption coefficient of the water. The ideal absorption coefficient of the water (a data D10 indicating the absorption coefficient of the water) is also outputted to the absorption coefficient calibration amount calculator 44 and the calibration data server 5 (Step S1208).

Figure 14:
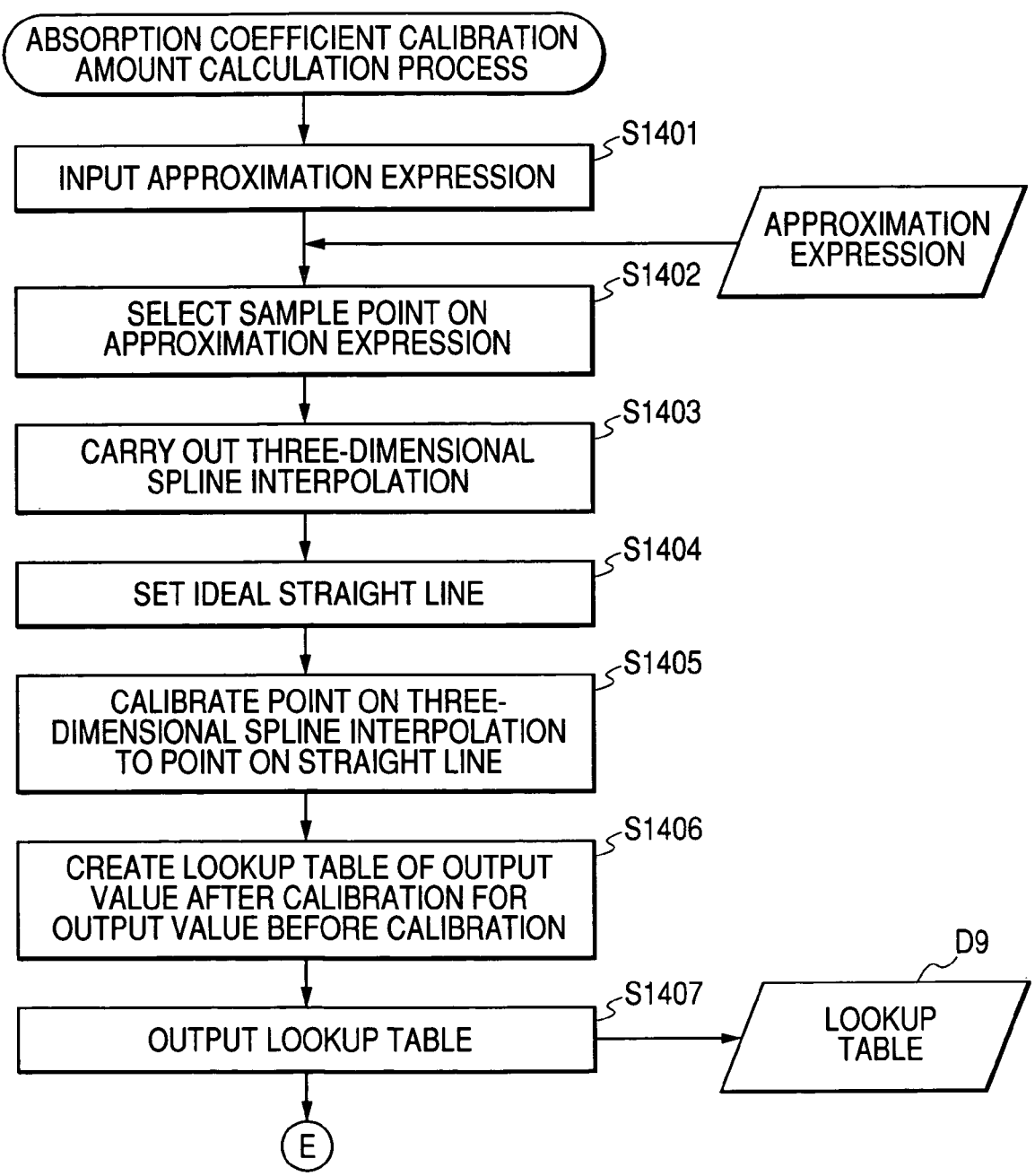
FIG. 14 is a flow chart showing the first embodiment of the present invention and explaining an example of a calculation process for obtaining an absorption coefficient calibration amount.

Referring back to FIG. 4, the absorption coefficient calibration amount calculator 44 receives the approximation expression that approximates the relation of the output value (LOG (output value)) to the penetration thickness, which is obtained from the result of the absorption coefficient calculation process in the absorption coefficient calculator 43 and carries out the absorption coefficient calibration amount calculation process for calculating the calibration amount of the absorption coefficient. Here, an example of the absorption coefficient calibration amount calculation process executed by the absorption coefficient calibration amount calculator 44 is explained using a flow chart of FIG. 14.

Figure 13C:
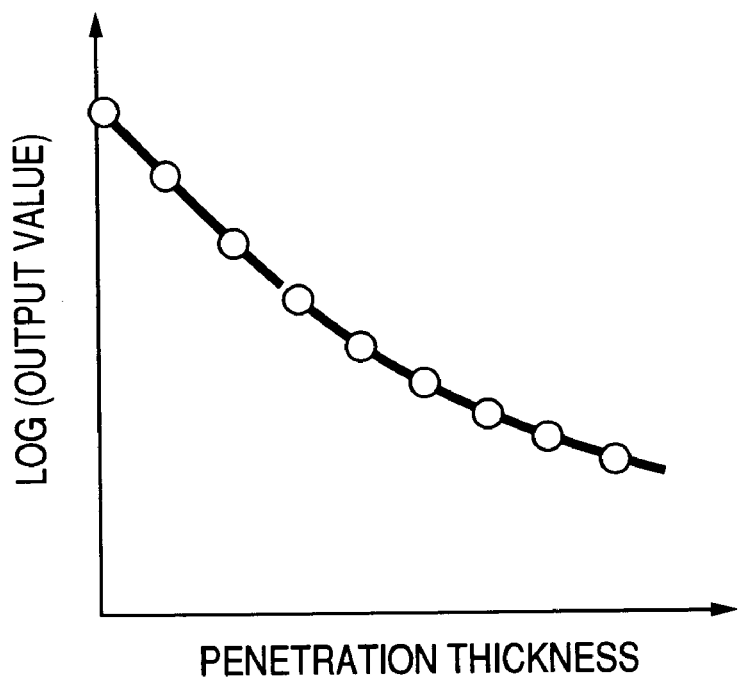
FIG. 13C is a diagram showing the first embodiment of the present invention and showing an example of a sample point on the approximation expression indicating the relation between the output value and the penetration thickness.

At first, the approximation expression that approximates the relation of the output value (LOG (output value)) to the penetration thickness is inputted (Step S1401). Next, as shown in FIG. 13C, a sample point on the approximation expression is selected (a white circle of FIG. 13C). This sample point is extracted from the portion on the straight line as well as on the portion of the cubic equation in the approximation expression. This sample point is used to carry out the cubic spline interpolation (Step S1403).

Figure 13D:
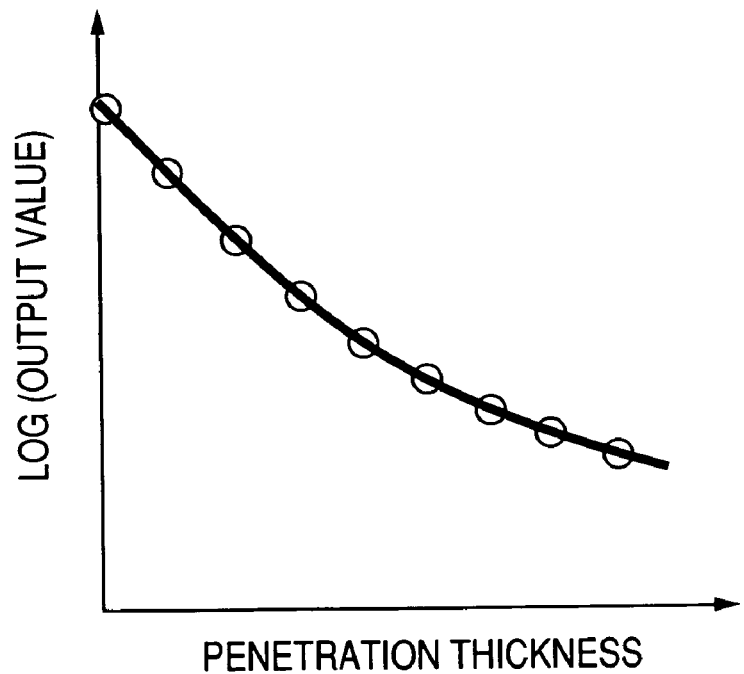
FIG. 13D is a diagram showing the first embodiment of the present invention and showing an example of a three-dimensional spline interpolation equation indicating the relation between the output value and the penetration thickness.

Consequently, as shown in FIG. 13D, the cubic spline interpolation equation is completed which represents the relation of the output value (LOG (output value)) to the penetration thickness where the boundary between the cubic equation and the linear equation is smoothly connected.

Figure 13E:
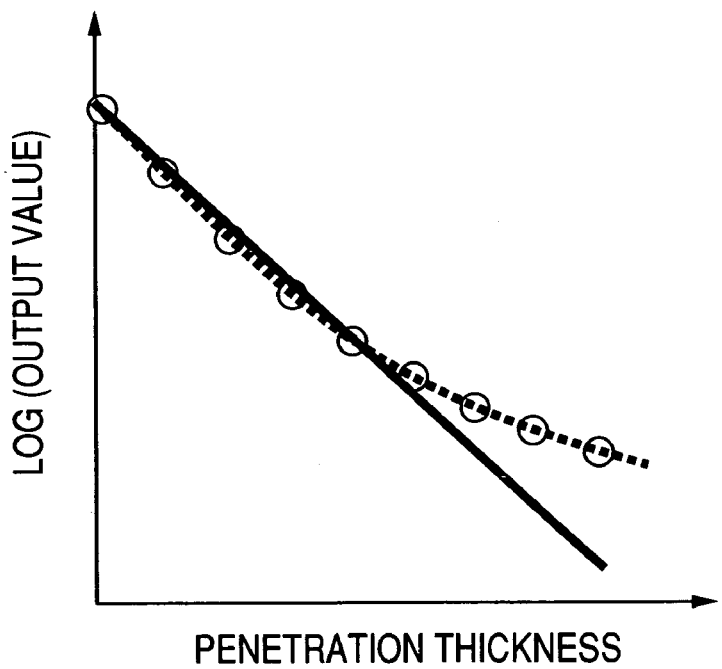
FIG. 13E is a diagram showing the first embodiment of the present invention and showing an example of an ideal straight line with respect to the approximation expression indicating the relation between the output value and the penetration thickness.
Figure 13F:
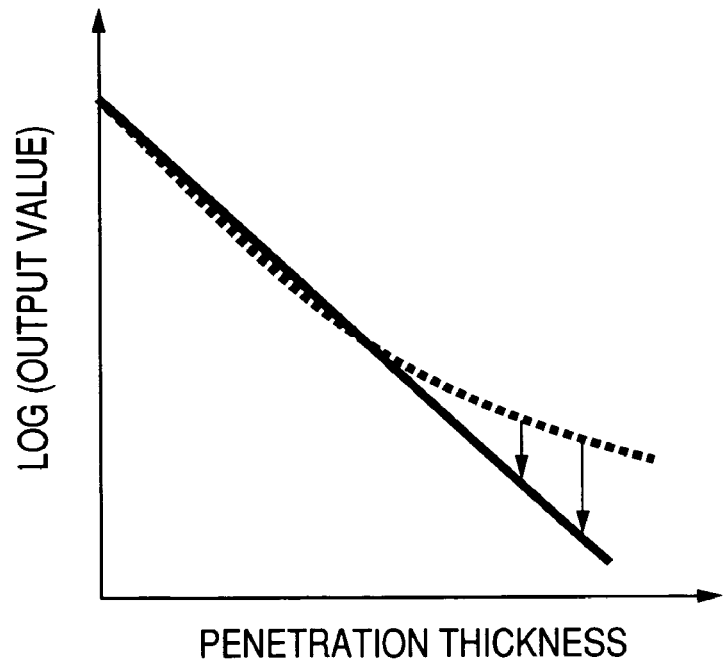
FIG. 13F is a diagram showing the first embodiment of the present invention and showing an example of the relation between the output value and the penetration thickness.

Next, the straight line portion of the approximation expression representing the relation of the output value (LOG (output value)) to the penetration thickness inputted at the step S1401 is set as the ideal straight line, and this ideal straight line is extended as shown in FIG. 13E (Step S1404). This ideal straight line represents the relation where the input X-rays were the mono-chromatic X-rays. That is, this ideal straight line represents that the attenuation caused by the water does not result from the penetration thickness. Hence, as shown in FIG. 13F, the point on the cubic spline interpolation equation at a certain penetration thickness is converted into a point on the ideal straight line at the same penetration thickness. That is, the output value is converted (calibrated) into the output value where the attenuation does not result from the penetration thickness (Step S1405).

Figure 13G:
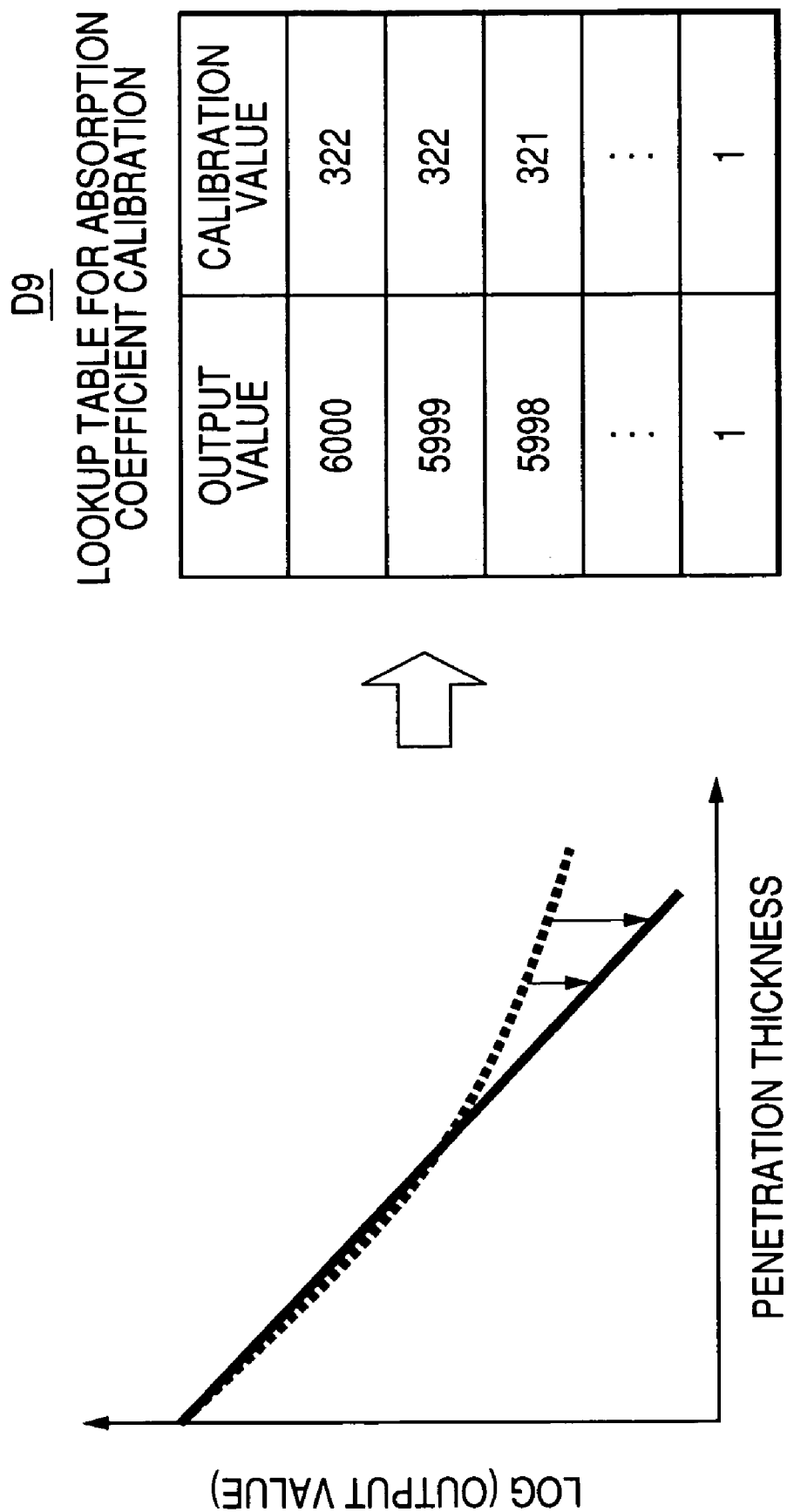
FIG. 13G is a diagram showing the first embodiment of the present invention and showing an example of a lookup table for an absorption coefficient calibration.

Then, as shown in FIG. 13G, the value into which the output value before this calibration is converted (namely, the relation between the output value before the calibration and the output value after the calibration) is tabled (Step S1406). At this time, in order to carry out the calibration process of the projection data at a high speed, instead of using the output value of the logarithm, an exponential is taken of the output value of this logarithm, and the table is generated in the state where it is returned back to the usual output value. This becomes an absorption coefficient calibration lookup table (LUT) D9. Then, the absorption coefficient calibration lookup table D9 is outputted to the calibration data server 5 (Step S1407).

As mentioned above, the property calculator 4 generates the absorption coefficient calibration lookup table D9 and the ideal absorption coefficient of the water (the data D10 indicating the absorption coefficient of the water), as the beam hardening calibration data D4.

As explained above, in this embodiment, the center tomographic image 801 (the three-dimensional reconstruction data D8) reconstructed parallel to the center line CL of the projection data D6 of the water phantom 31 and the tube 2a is read from the image data server 6, and the two-dimensional modeling is performed on the read center tomographic image 801 which is assumed to be the circle, and the radius of the two-dimensionally modeled circle and the coordinate of the center are used to re-arrange the tube 2a, the sensor 2b and the modeled circle (the center tomographic image 801). Then, the intersects of the re-arranged circle and the path PH until the X-rays arrive at the sensor 2b from the tube 2a are determined to then determine the penetration thickness of the water phantom 31 from the intersects A, B. Consequently, in order to accurately determine the attenuation property when the X-rays are penetrated through the subject 1, the larger quantity of the data of the output values of the sensors 2b with respect to the penetration thicknesses can be gathered easier. Thus, the larger quantity of the data of the output values of the sensors 2b with respect to the penetration thicknesses can be obtained, thereby accurately determining the absorption coefficient calibration lookup table D9 of the subject 1 and the ideal absorption coefficient of the subject 1.

Also, when the X-ray CT image photographing is carried out, the water phantom 31 is always imaged in order to carry out the water calibration (the work for converting into the CT value). Thus, the projection data D6 of the imaged water phantom 31 can be again used to generate the absorption coefficient calibration lookup table D9 and the ideal absorption coefficient of the water (the data D10 indicating the absorption coefficient of the water), and the projection data D6 of the water phantom 31 can be effectively used in the operation other than the water calibration.

Second Embodiment

A second embodiment of the present invention will be described below. This embodiment differs from the first embodiment only in the process in the property calculator 4. Thus, in the following explanations, the detailed explanations are omitted for the same parts as those of the first embodiment.

In the first embodiment, the penetration thickness of the X-ray is calculated on the two-dimensional flat surface, and the absorption coefficient calibration lookup table D9 is generated. On the contrary, this embodiment is designed such that the penetration thickness of the X-ray is calculated in a three-dimensional space, and the absorption coefficient calibration lookup table (LUT) is generated.

Although the functional configuration of the property calculator 4 is similar to that shown in FIG. 4, the contents of processes carried out in respective devices 41 to 44 are different from those of the first embodiment.

Figure 15:
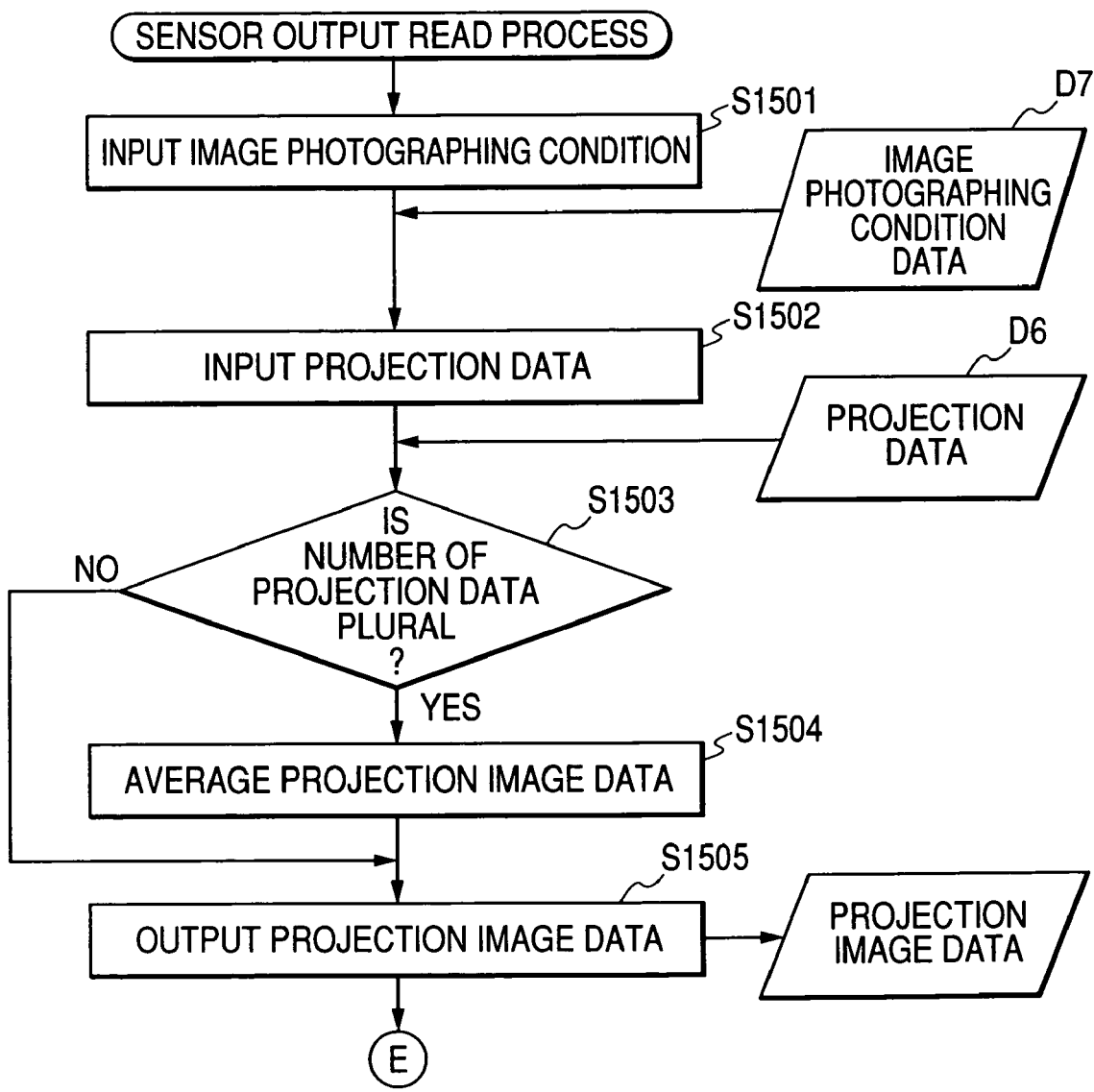
FIG. 15 is a flow chart showing a second embodiment of the present invention and explaining an example of a sensor output read process.

At first, the sensor output read process carried out by the sensor output value reader 41 is explained. In the first embodiment, the sensor output value reader 41 generates the projection line data. However, in the calculation of the three-dimensional space, since the data only for one line is insufficient, all lines of the sensors 2b are used as the projection image data. Thus, the sensor output read process in this embodiment is executed in accordance with a flow chart shown in FIG. 15.

At first, the image photographing condition data D7 when the water phantom 31 is imaged is inputted (Step S1501). Then, the projection data D6 is inputted (Step S1502). Next, whether or not the number of the inputs of the projection data D6 is 2 or more is judged (Step S1503). If the number of the inputs is 1, the input projection data D6 is outputted in its original state as the projection image data (Step S1505). On the other hand, if the number of the inputs is 2 or more, the plurality of projection image data D7 are averaged for each pixel (Step S1504), and the averaged projection image data is outputted (Step S1505).

Figure 16:
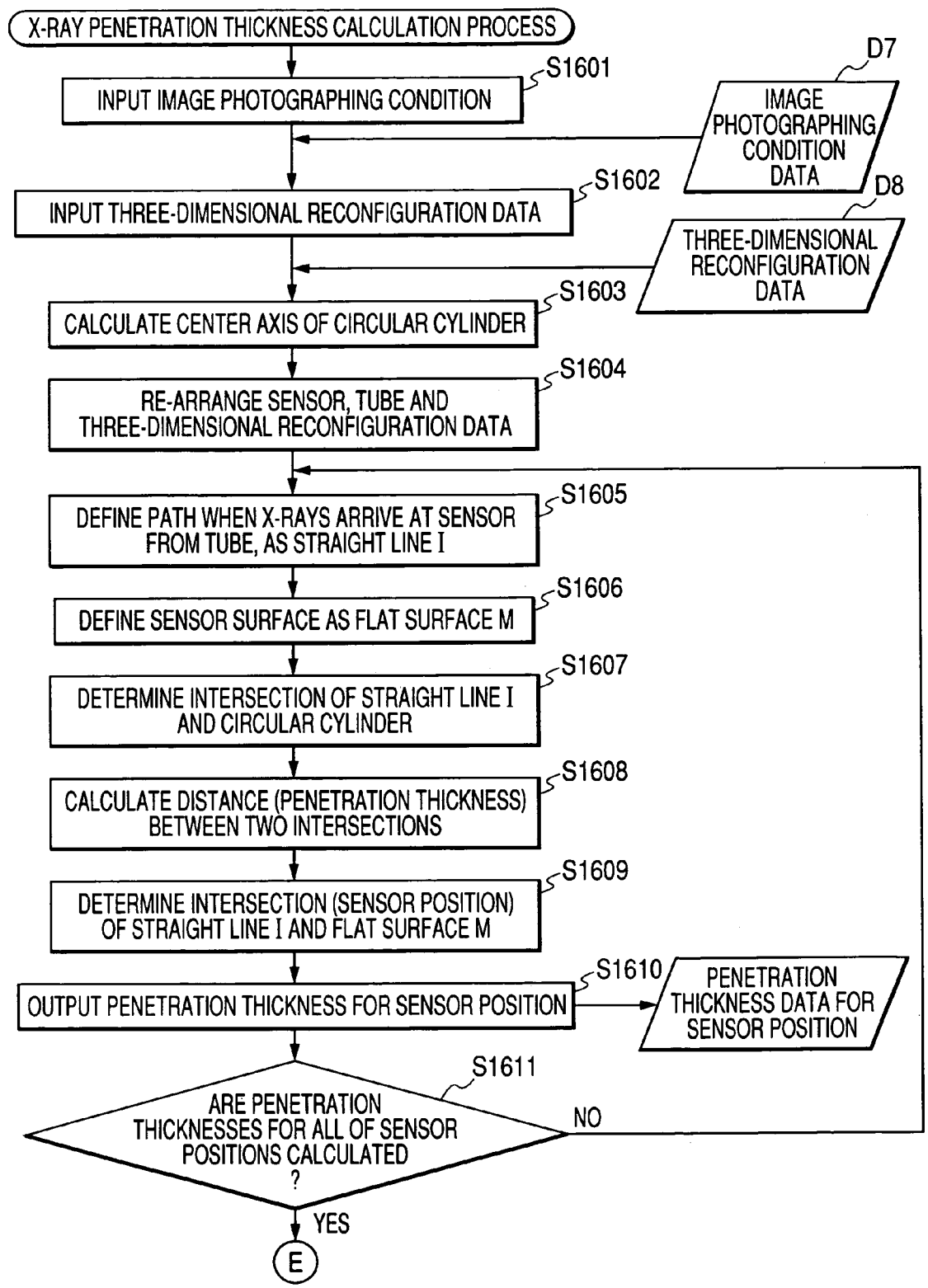
FIG. 16 is a flow chart showing the second embodiment of the present invention and explaining an example of a calculation process for obtaining X-ray penetration thickness.

The X-ray penetration thickness calculation process carried out by the X-ray penetration thickness calculator 41 will be described below. An example of the X-ray penetration thickness calculation process carried out in this embodiment will be described below with reference to a flow chart of FIG. 16.

At first, the image photographing condition data D7 when the water phantom 31 is imaged is inputted (Step S1601). Next, the three-dimensional reconstruction data D8 is inputted (Step S1602).

Then, the central axis of the circular cylinder where the water phantom 31 is three-dimensionally modeled is determined (Step S1603). How to determine the central axis of the circular cylinder where the water phantom 31 is three-dimensionally modeled is explained using FIGS. 17A to 17C.

Figure 17A:
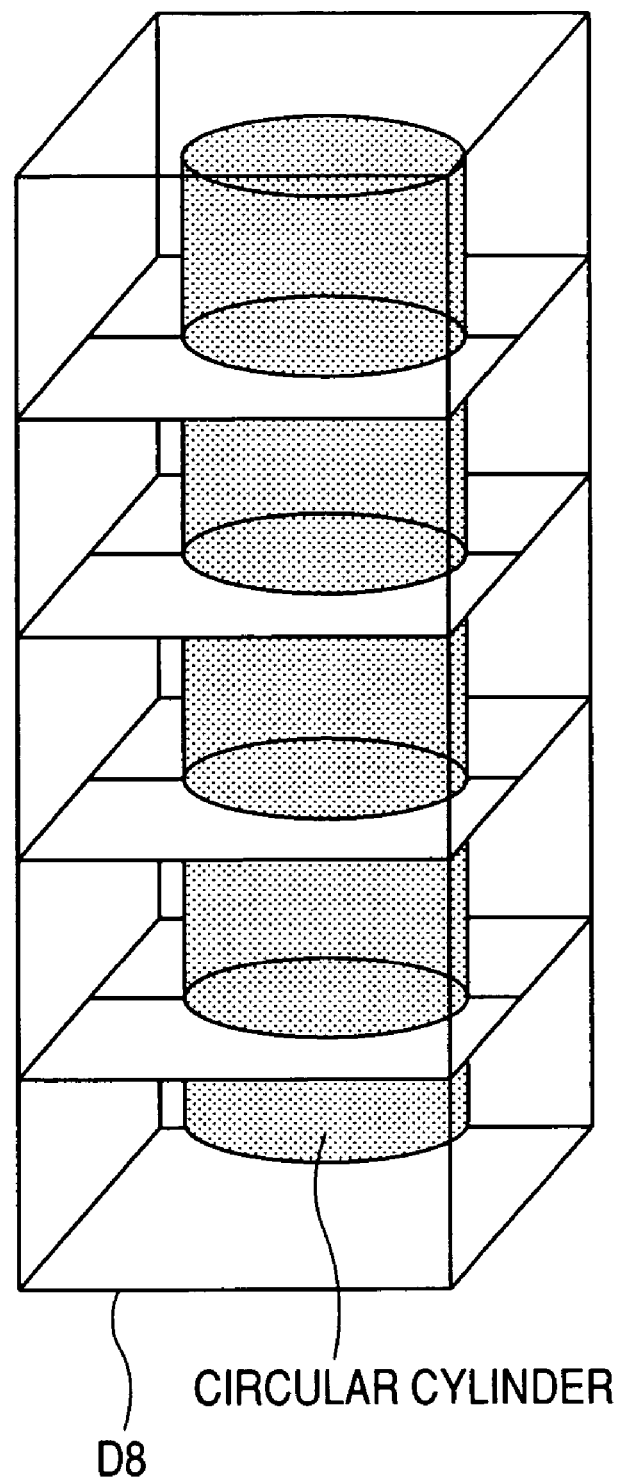
FIGS. 17A, 17B and 17C are diagrams showing the second embodiment of the present invention and showing an example of a three-dimensional reconstruction data, a center of a tomographic image, and a central axis of a circular cylinder on which a water phantom is three-dimensionally modeled.
Figure 17B:
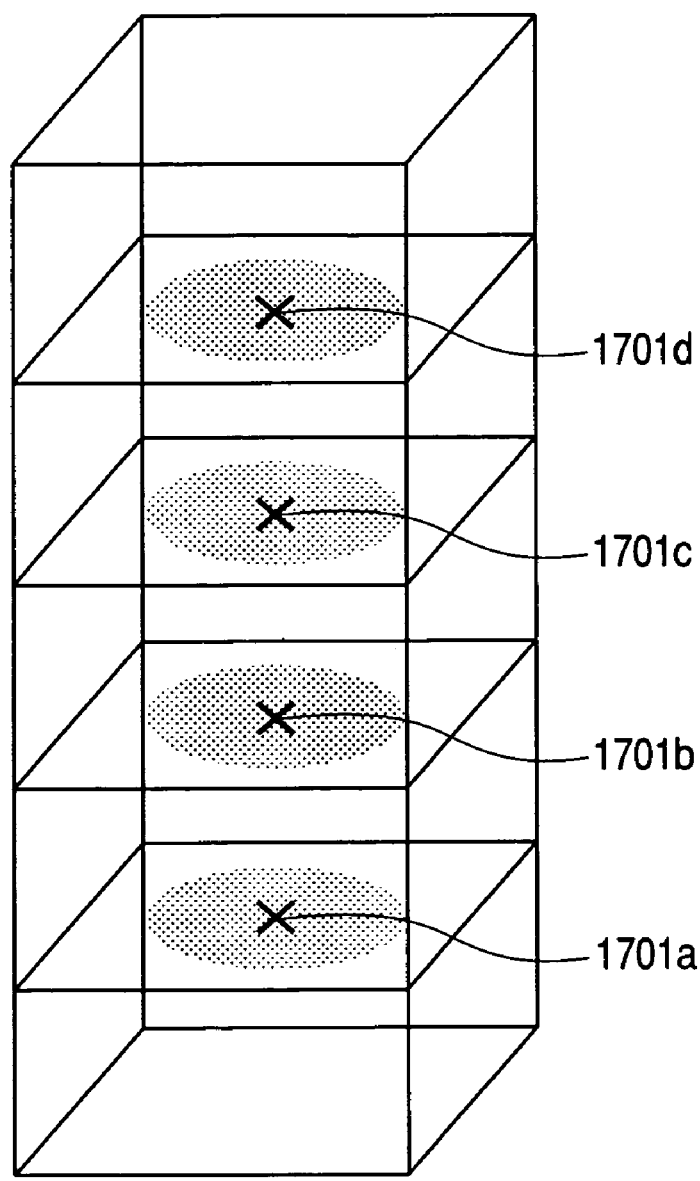
Figure 17C:
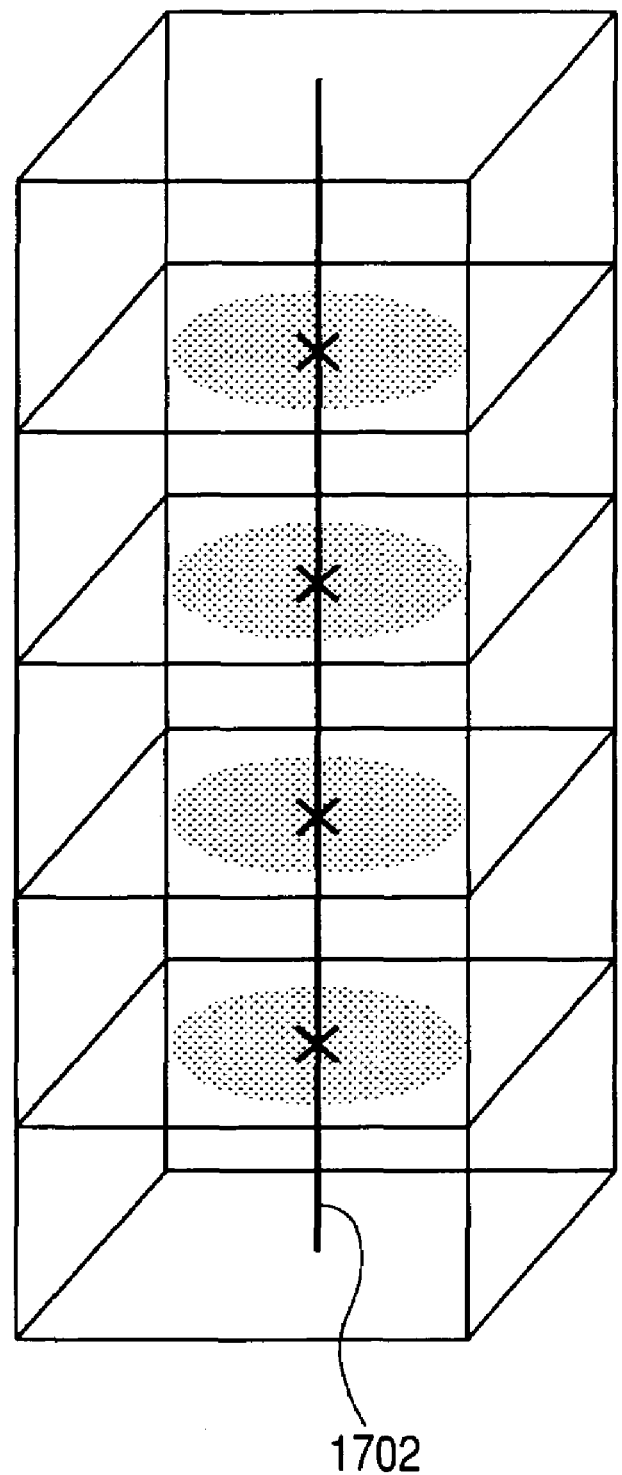

FIG. 17A is a diagram showing an example of the three-dimensional reconstruction data D8. A plurality of tomographic images in the same direction are obtained from the three-dimensional reconstruction data D8. Then, for the obtained tomographic images, circular centers 1701a to 1701d are determined as shown in FIG. 17B. A method of determining the circular centers 1701a to 1701d is based on the method of determining the circle center based on the two-dimensional modeling. Here, if the two-dimensional modeling through the ellipse is the more accurate representation, the tomographic image may be approximated through the ellipse without using the circle. Then, as shown in FIG. 17C, when a straight line 1702 passing through the circular centers 1701*a* to 1701*d* obtained from the plurality of tomographic images is determined, the straight line 1702 becomes the central axis of the circular cylinder.

Referring back to FIG. 16, the sensor 2*b*, the tube 2*a* and the three-dimensional reconstruction data (namely, the circular cylinder) D8 of the water phantom 31 are re-arranged (Step S1604). In the re-arrangement, an error (three-dimensional error) between the central axis of the three-dimensional reconstruction data D8 and the central axis of the three-dimensional reconstruction data of the water phantom 31 is calculated.

Figure 18A:
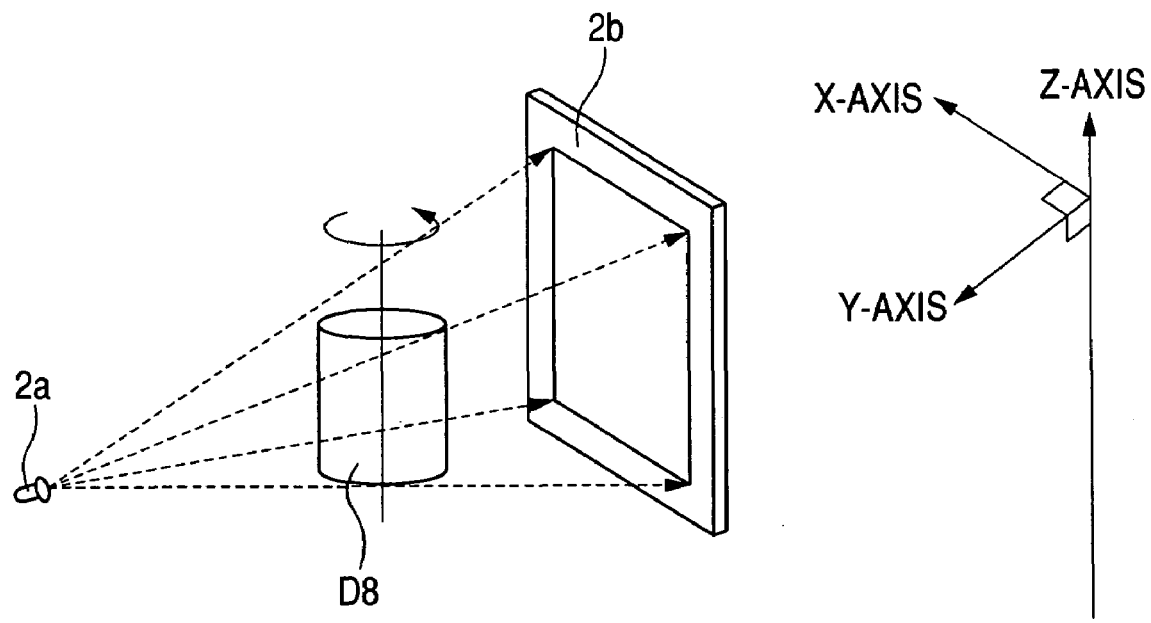
FIGS. 18A, 18B and 18C are diagrams showing the second embodiment of the present invention and showing a first stage in re-arranging a sensor, a tube, and a three-dimensional reconstruction data of the water phantom.

FIGS. 18A, 18C, 18C, 19A and 19B show an example of the manner of re-arranging the sensor 2*b*, the tube 2*a* and the three-dimensional reconstruction data D8 of the water phantom 31. FIG. 18A is a diagram showing how to set the X-Y-Z axis of the space used in the re-arrangement. This setting of the X-Y-Z axis is also similar in the other drawings.

Figure 18B:
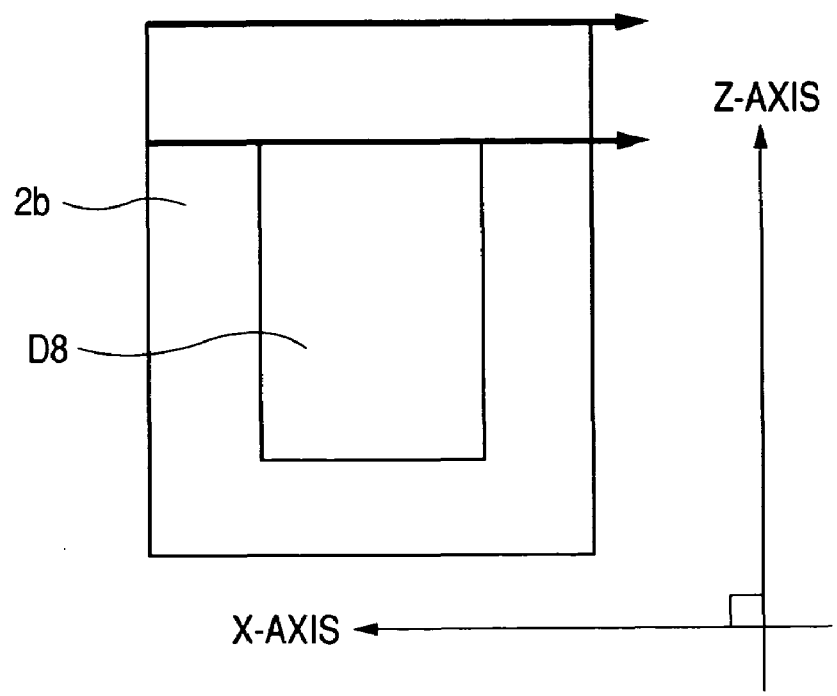
Figure 18C:
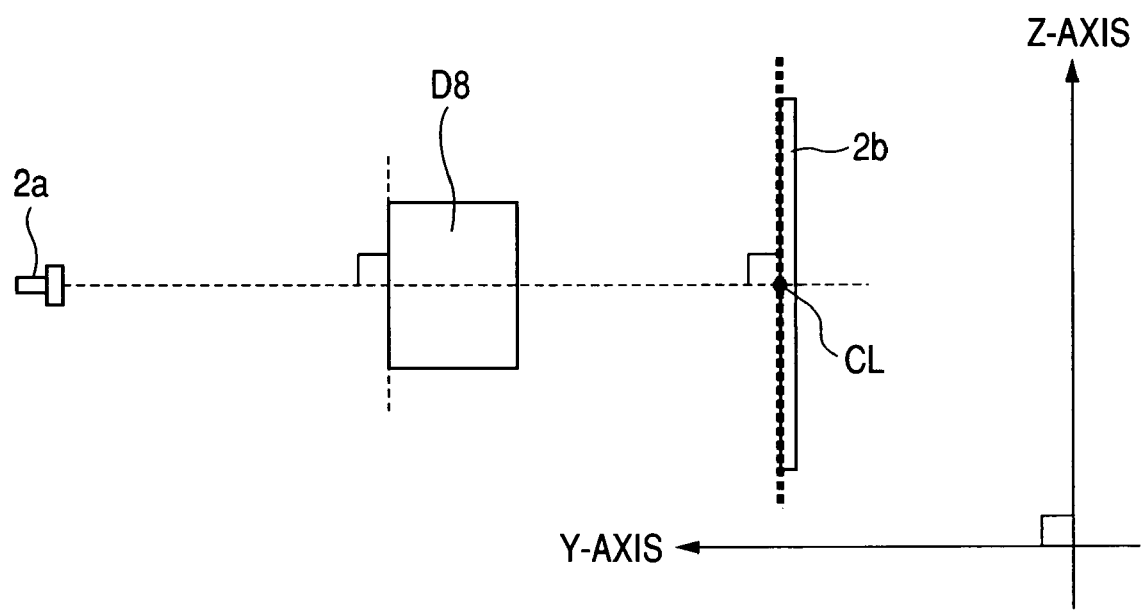
Figure 19A:
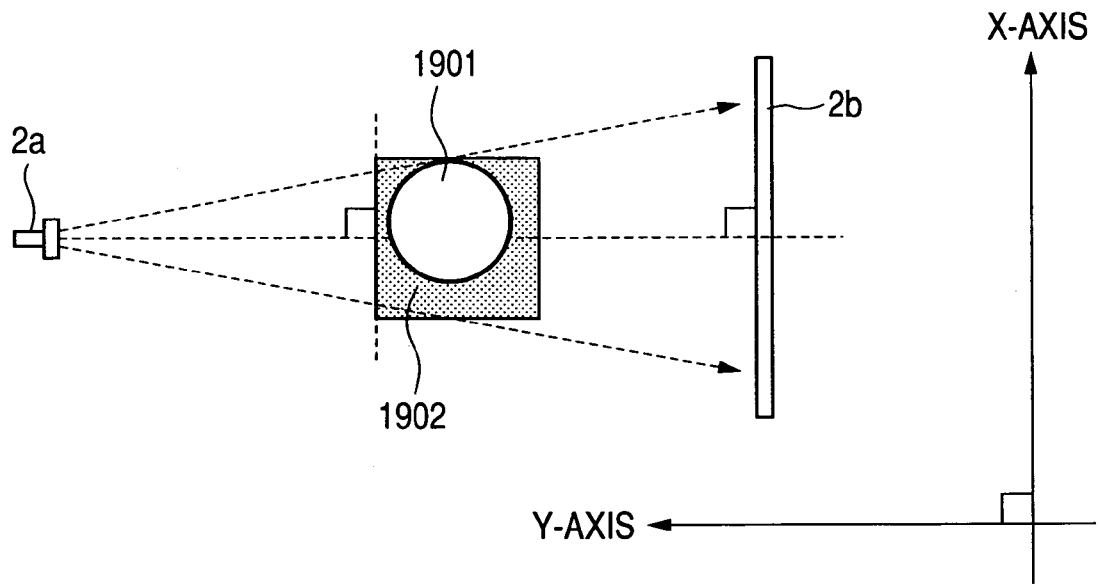
FIGS. 19A and 19B are diagrams showing the second embodiment of the present invention and showing a second stage in re-arranging the sensor, the tube, and the three-dimensional reconstruction data of the water phantom.
Figure 19B:
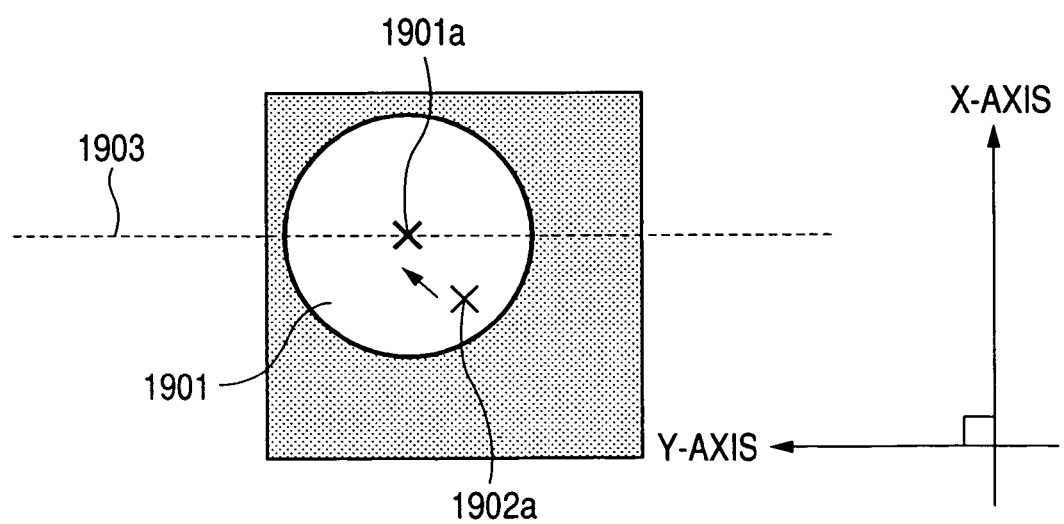

As shown in FIG. 18B, in such a way that the sensor 2*b* and the three-dimensional reconstruction data D8 of the water phantom 31 are parallel to the X-axis on the X-Z axis surface, the three-dimensional reconstruction data D8 of the water phantom 31 is re-arranged at a position determined by the image photographing condition data D7. Moreover, as shown in FIG. 18C, in such a way that the sensor 2*b* and the three-dimensional reconstruction data D8 of the water phantom 31 are parallel to the Z-axis on the Y-Z axis surface, the three-dimensional reconstruction data D8 of the water phantom 31 is re-arranged at a position determined by the image photographing condition data D7. Then, as shown in FIGS. 19A and 19B, the three-dimensional reconstruction data D8 of the water phantom 31 is re-arranged such that a center 1901a (namely, the center of the circle) of a tomographic image 1901 of the water phantom 31 is put on a plane parallel to a Y-Z axis plane 1903 including a straight line through which the center of the sensor 2*b* and the tube 2*a* are connected perpendicularly (in the Y-axis direction).

Next, the penetration thickness is calculated. At first, a path until the X-rays arrive at the sensor 2*b* from the tube 2*a* is defined as a straight line I (Step S1605). Then, a surface of the sensor 2*b* is defined as a flat plane M (Step S1606). If the further accurate representation is attained when the surface of the sensor 2*b* is represented as a curved surface, the surface of the sensor 2*b* may be defined as a curved plane M'.

Moreover, the intersection of the straight line I and the circular cylinder where a tomographic image 1902 is modeled is determined (Step S1607). This intersection can be determined by solving a cubic equation.

Then, calculating the distance between the determined two intersections finds the penetration thickness (Step S1608). Moreover, an intersection of the straight line I and the flat surface M or the curved surface M' is determined (Step S1609). This intersection is also determined by solving a cubic equation. The thus-determined intersection becomes the position of the sensor 2*b* with respect to the penetration thickness. Then, the penetration thickness data with respect to the position of this sensor 2*b* is outputted (Step S1610). Then, whether or not the penetration thickness is calculated with respect to all of the positions of the sensors 2*b* is judged (Step S1611). For all of the positions of the sensors 2*b*, the processes of the steps S1605 to S1610 are repeated until the execution of the calculation of the penetration thickness. However, it is not always necessary to perform the calculation of the penetration thickness on all of the positions of the sensors 2*b*. It is allowable to repeat the processes of the steps S1605 to S1610 until the obtainment of the necessary data.

Figure 20:
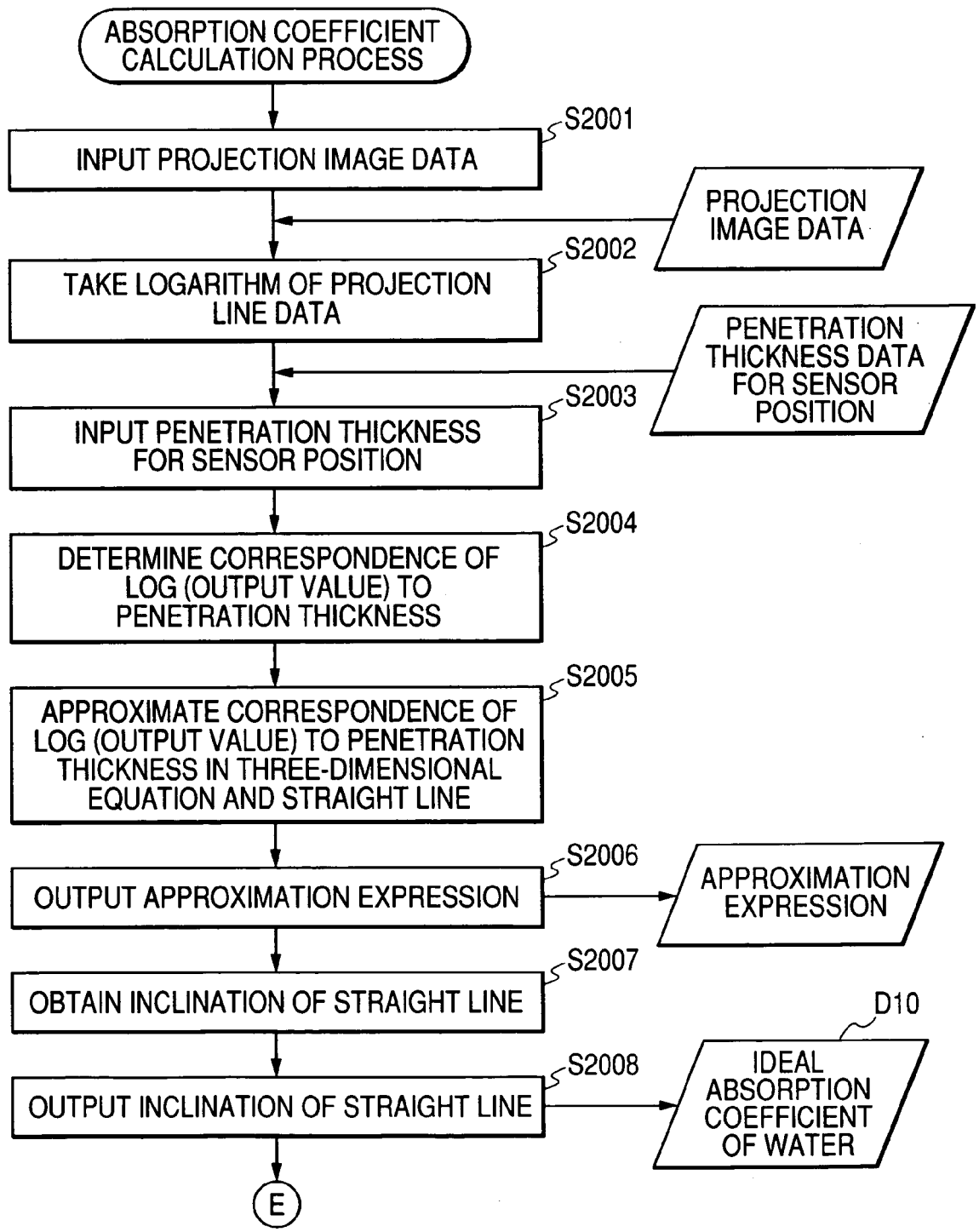
FIG. 20 is a flow chart showing the second embodiment of the present invention and showing an example of an absorption coefficient calculation process.

The thus-obtained data of the penetration thickness with respect to the position of the sensor 2*b* is used to carry out the absorption coefficient calculation process. The absorption coefficient calculation process in this embodiment is not basically different from that of the first embodiment explained by using the flow chart of FIG. 12. However, a part of the input data is different from the first embodiment. In the first embodiment, the projection line data is inputted at the step S1201. However, in this embodiment, this projection line data becomes the projection image data. Thus, the content of the absorption coefficient calculation process in this embodiment is illustrated in a flow chart shown in FIG. 20. As mentioned above, in FIG. 20, the processes except a step S2001 of inputting the projection image data are equal to those of the flow chart shown in FIG. 12. Hence, their explanations are omitted.

Finally, the absorption coefficient calibration amount calculation process is executed. The absorption coefficient calibration amount calculation process in this embodiment is not different from the absorption coefficient calibration amount calculation process of the first embodiment explained by using the flow chart of FIG. 14. Thus, their explanations are omitted.

In this way, the property calculator 4 generates the lookup table for the absorption coefficient calibration and the ideal absorption coefficient of the water, as the data for the beam hardening calibration.

As mentioned above, even if the penetration thickness of the X-rays is calculated in the three-dimensional space, it is possible to obtain the effect similar to that of the first embodiment.

Note that, in the first and second embodiments, attention is paid to the usage of the projection data D6 of the water phantom 31 for the sake of the water calibration, and the case of image photographing the water phantom 31 is explained. Such design is preferable because the projection data D6 of the water phantom 31 can be effectively used. However, any material other than the water can be also used. For example, a circular cylinder made of acryl can be used to determine the attenuation property of the acryl, or a circular cylinder made of calcium can be imaged to determine the attenuation property of the calcium. Since the acryl has the absorption coefficient substantially similar to that of the water, it can be used instead of the absorption coefficient of the water. Also, the attenuation property of the calcium can be used in considering an attenuation property of a bone.

Also, the water phantom 31, which is assumed to be the circular cylinder, is three-dimensionally modeled to generate the absorption coefficient calibration lookup table D9. However, depending on the shape of the water phantom 31, there is a case where a better result may be obtained when the three-dimensional modeling is performed on an ellipsoidal cylinder or polygonal cylinder and not on the circular cylinder. FIGS. 21A to 21F show examples of the shapes of the water phantom.

Figure 21A:
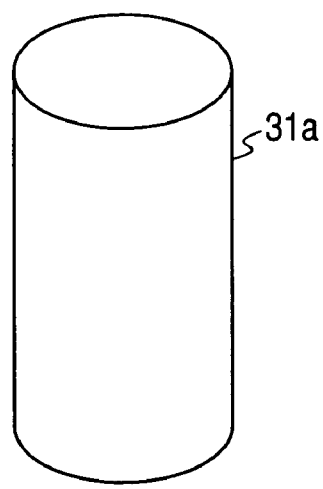
FIGS. 21A, 21B; 21C, 21D, 21E and 21F are diagrams showing an embodiment of the present invention and showing an example of a shape of a water phantom.

A water phantom 31*a* shown in FIG. 21A has a shape of a circular cylinder. Thus, it is preferable that the tomographic image, which is obtained from the circular cylinder after the execution of the three-dimensional modeling on the circular cylinder, be two-dimensionally modeled on a circle or ellipse.

Figure 21B:
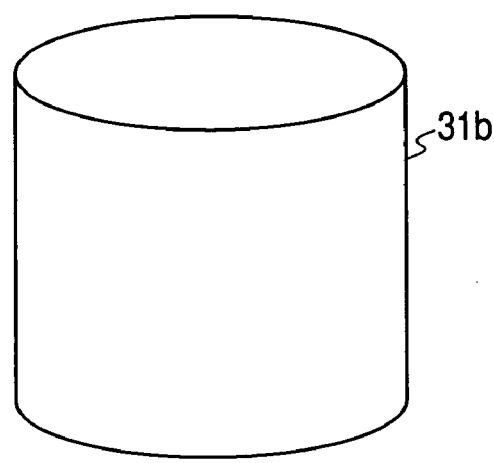

A water phantom 31*b* shown in FIG. 21B has a shape of an ellipsoidal cylinder. Thus, it is preferable that the tomographic image, which is obtained from the ellipsoidal cylinder after the execution of the three-dimensional modeling on the ellipsoidal cylinder, be two-dimensionally modeled on a circle or ellipse.

Figure 21C:
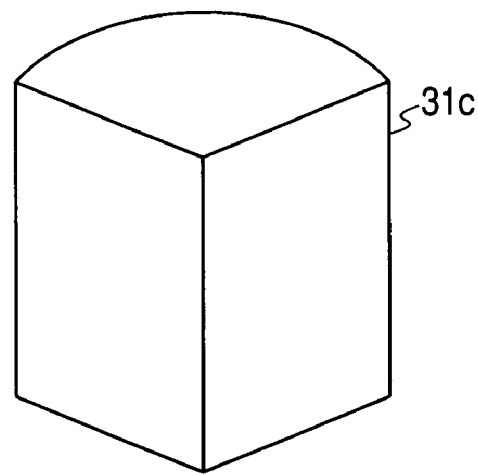

A water phantom 31c shown in FIG. 21C has a shape of a sector cylinder. Thus, it is preferable that the tomographic image, which is obtained from the sector cylinder after the execution of the three-dimensional modeling on a sector cylinder, be two-dimensionally modeled on a sector.

Figure 21D:
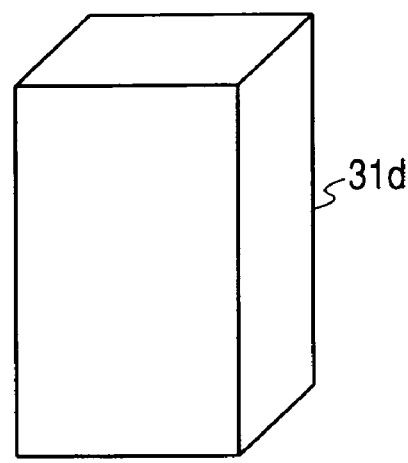

A water phantom 31d shown in FIG. 21D has a shape of a square pole. Thus, it is preferable that the tomographic image, which is obtained from the square pole after the execution of the three-dimensional modeling on a square cylinder, be two-dimensionally modeled on a quadrangle.

Figure 21E:
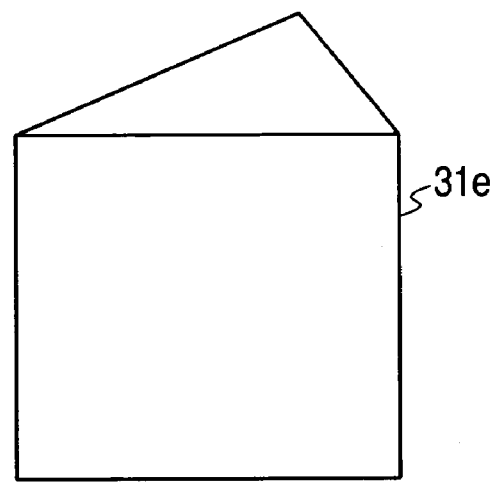

A water phantom 31e shown in FIG. 21E has a shape of a triangle pole. Thus, it is preferable that the tomographic image, which is obtained from the triangle pole after the execution of the three-dimensional modeling on the triangle pole, be two-dimensionally modeled on a triangle.

Figure 21F:
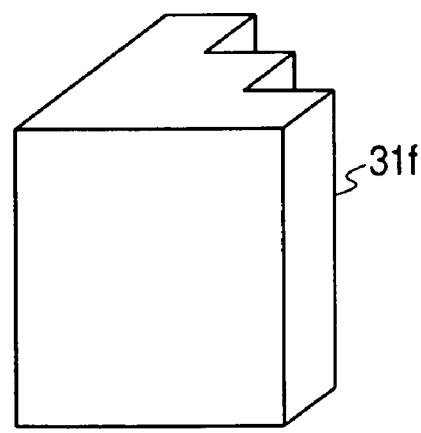
Figure 23A:
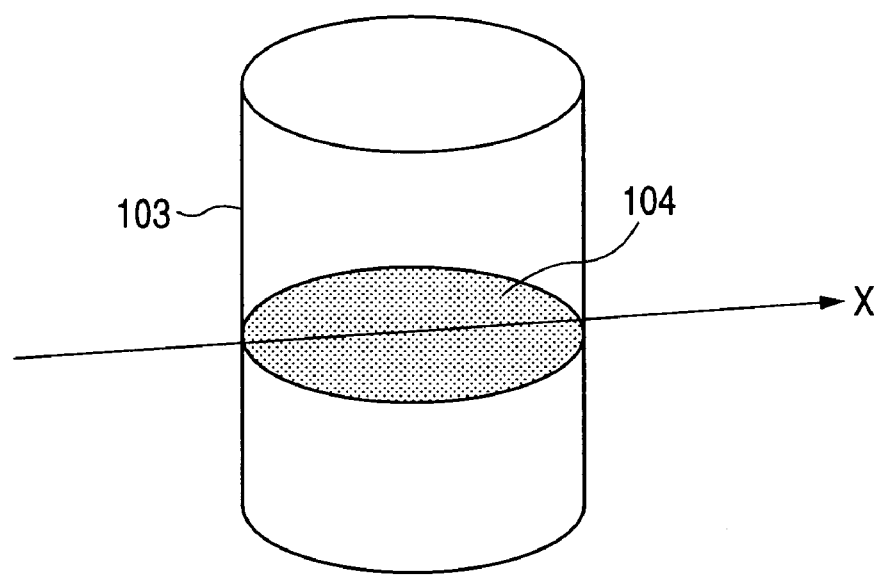
FIGS. 23A and 23B are diagrams showing a relation between a radiation absorption coefficient and the penetration thickness.
Figure 23B:
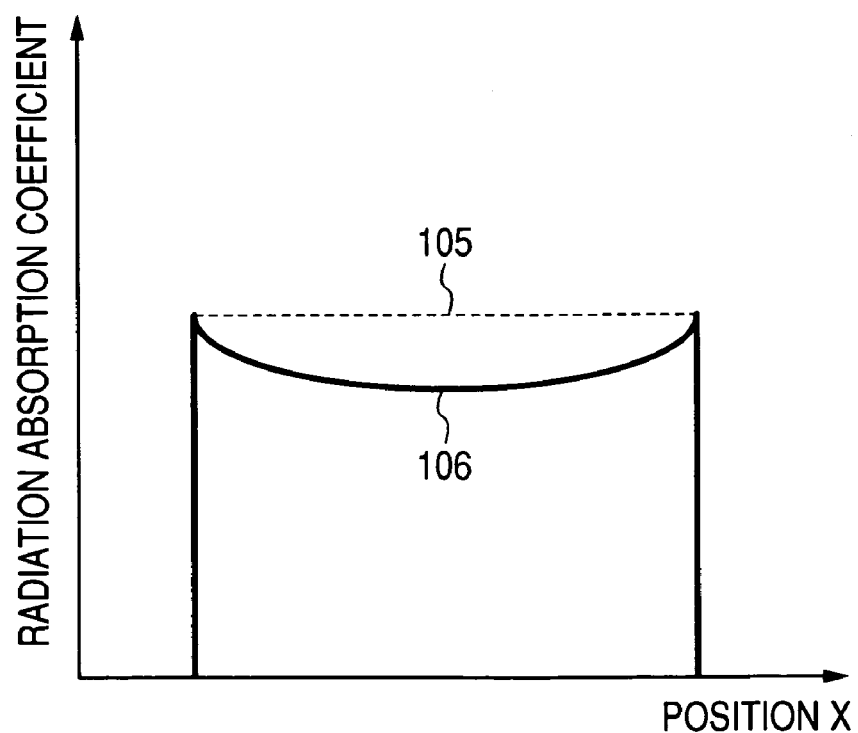

A water phantom 31f shown in FIG. 21F is a polygonal cylinder having a shape of stages. Thus, it is preferable that the tomographic image, which is obtained from the polygonal cylinder after the execution of the three-dimensional modeling on the polygonal cylinder having the shape of the stages, be two-dimensionally modeled on the polygon having the shape of the stages. Note that, in the case of carrying out the three-dimensional modeling on the polygonal cylinder, the central axis of the polygonal cylinder and the center of the polygon that is the tomographic image of the polygonal cylinder point out all elements of a center of gravity, an inner center, a circum-center, and an orthocenter.

(Other Embodiments of the Invention)

The embodying method, which in order to operate the various devices so as to attain the functions of the embodiments as mentioned above, sends the program codes of the software for attaining the functions of the embodiments to the computers in the apparatuses or systems connected to the various devices, and operates the various devices in accordance with the programs stored in the computers (CPU or MPU) of the systems or apparatuses is also included in the range of the present invention.

Also, in this case, the program codes themselves of the software attains the function of the embodiments as mentioned above. Then, the program code themselves and means for sending the program code to the computer, for example, the record medium for storing the program code constitute the present invention. As the record medium for storing the program code, for example, it is possible to use a flexible disc, a hard disc, an optical disc, a magneto-optic disc, a CD-ROM, a magnetic tape, a non-volatile memory card, or an ROM.

Also, not only in the case where since the computer executes the sent program code, the function of the embodiment is attained, but also in the case where the function of the embodiment is attained by the joint operation between the program code and the operating system (OS) or other application software which is operated in the computer, it is needless to say that the program code is included in the embodiments of the present invention.

Moreover, in the case where, after the sent program code is stored in a memory contained in a function expansion board of the computer or a function expansion unit connected to the computer, CPU or the like installed in the function expansion board or function expansion unit carries out a part or whole of the actual process based on an instruction of the program code, and the function of the embodiment as mentioned above is attained by the process, it is needless to say that the case is included in the present invention.

This application claims priority from Japanese Patent Application No. 2004-257623 filed Sep. 3, 2004, which is hereby incorporated by reference herein.

What is claimed is:

1. An information processor, comprising:
    output value reading means for reading an output value of a sensor where a projection data of an object is generated:
    penetration thickness calculating means for calculating a penetration thickness of a radiation penetrated through the object by using a three-dimensional reconstruction image data reconstructed in accordance with the projection data of the object: and
    calibration amount calculating means for calculating a calibration amount calibrate an absorption coefficient of the radiation in the object by using a correspondence between the output value of the sensor and the penetration thickness of the radiation.

2. An information processor according to claim 1, wherein said penetration thickness calculation means three-dimensionally models the object on a circular cylinder, an ellipsoidal cylinder, or a polygonal cylinder; and uses the object modeled on a circular cylinder, an elliptic cylinder, or a polygonal cylinder together with the three-dimensional reconstruction image data to calculate the penetration thickness of the radiation penetrated through the object.

3. An information processor according to claim 2, wherein said penetration thickness calculating means determines a central axis of the circular cylinder, the ellipsoidal cylinder, or the polygonal cylinder; determines a three-dimensional error between the central axis determined and a central axis of the three-dimensional reconstruction image data; and calculates the penetration thickness of the radiation penetrated through the object, in accordance with the three-dimensional error determined.

4. An information processor according to claim 1, wherein said penetration thickness calculating means two-dimensionally models a tomographic image obtained from the three-dimensional reconstruction image data on a circle, an ellipse, or a polygon, and uses the tomographic image modeled on a circle, an ellipse, or a polygon to calculate the penetration thickness of the radiation penetrated through the object.

5. An information processor according to claim 4, wherein said penetration thickness calculating means extracts an edge of the tomographic image obtained from the three-dimensional reconstruction image data to generate an edge image indicating the edge of the tomographic image extracted, and employs a circle, an ellipse, or a polygon having the smallest error with respect to the edge image generated, as a circle, an ellipse, or a polygon on which the tomographic image is modeled.

6. An information processor according to claim 5, wherein said penetration thickness calculating means converts the tomographic image obtained from the three-dimensional reconstruction image data into a binary value to generate a binary image, and uses the binary image generated to extract the edge of the tomographic image.

7. An information processor according to claim 4, wherein said penetration thickness calculating means determines a center and a radius of the circle to two-dimensionally model the tomographic image.

8. An information processor according to claim 4, wherein said penetration thickness calculating means determines a minor axis and a major axis of the ellipse to two-dimensionally model the tomographic image.

9. An information processor according to claim 4, wherein said penetration thickness calculating means determines a center and a length of sides of the polygon to two-dimensionally model the tomographic image.

10. An information processor according to claim 4, wherein said penetration thickness calculating means uses a two-dimensional error between a center of the circle, the ellipse, or the polygon and a center of the tomographic image obtained from the three-dimensional reconstruction image data to calculate the penetration thickness of the radiation penetrated through the object.

11. An information processor according to claim 3, wherein said penetration thickness calculating means re-arranges the circular cylinder, the ellipsoidal cylinder, or the polygonal cylinder, the sensor, and a tube for emitting the radiation within a same space, in accordance with the determined three-dimensional error, and determines the penetration thickness of the radiation penetrated through the circular cylinder, ellipsoidal cylinder, or polygonal cylinder re-arranged.

12. An information processor according to claim 10, wherein said penetration thickness calculating means re-arranges the circle, the ellipse or the polygon, the sensor, and a tube for emitting the radiation within the same space, in accordance with the determined three-dimensional error, and determines the penetration thickness of the radiation penetrated through the circle, ellipse or polygon re-arranged.

13. An information processor according to claim 11, wherein said penetration thickness calculating means solves a cubic equation to determine an intersection of a function, through which the sensor and the tube are connected, and the circular cylinder, the elliptic cylinder, or the polygonal cylinder, and determines, in accordance with the intersection determined, the penetration thickness of the radiation penetrated through the circular cylinder, elliptic cylinder, or polygonal cylinder re-arranged.

14. An information processor according to claim 12, wherein said penetration thickness calculating means solves a quadratic equation to determine an intersection of a function, through which the sensor and the tube are connected, and the circle, the ellipse or the polygon, and determines, in accordance with the intersection determined, the penetration thickness of the radiation penetrated through the circle, ellipse, or polygon re-arranged.

15. An information processor according to claim 1, wherein said calibration amount calculating means farther includes:
approximation means for determining an approximation expression to approximate a correspondence between the output value of the sensor and the penetration thickness of the radiation penetrated through the object:
absorption coefficient calculating means for determining an ideal absorption coefficient of the uniform object by using the approximation expression: and
calibration value generating means for generating a calibration function or a lookup table for calibrating the output value of the sensor such that the absorption coefficient of the object becomes the ideal absorption coefficient.

16. An information processor according to claim 15, wherein said approximation means takes a logarithm of the output value of the sensor, and approximates a correspondence between the output value of the sensor where the logarithm is taken and the penetration thickness of the radiation penetrated through the object, by using a low-order polynomial equation and a straight line.

17. An information processor according to claim 15, wherein said calibration value generating means converts the output value of the sensor in the low-order polynomial equation into the output value of the sensor in the straight line, and uses the converted output value of the sensor to generate a calibration function or a lookup table for calibrating the output value of the sensor.

18. An information processor according to claim 15, wherein said absorption coefficient calculating means sets a sampling point for the approximation expression, interpolates the sampling point by using a spline interpolation to interpolate the approximation expression by using the sampling point interpolated, and determines the ideal absorption coefficient of the object by using the interpolated approximation expression.

19. An information processor according to claim 1, said penetration thickness calculating means calculates the penetration thickness of the radiation penetrated through the object to reach the sensor.

20. An image photographing system, comprising:
the information processor according to claim 1:
an image photographing apparatus for image photographing the object by using the radiation: and
a reconstruction processor for generating a three-dimensional reconstruction data of the object,
wherein said reconstruction processor uses the calibration amount calculated by said object information processor to carry out a beam hardening calibration, and generates the three-dimensional reconstruction data of a subject by reflecting a result obtained through the beam hardening calibration.

21. An absorption coefficient calibration method, comprising the steps of:
reading an output value of a sensor in which a projection data of an object is generated:
calculating a penetration thickness of a radiation penetrated through the object by using a three-dimensional reconstruction image data reconstructed in accordance with a projection data of the object: and
calculating a calibration amount for calibrating an absorption coefficient of the radiation in the object by using a correspondence between the output value of the sensor and the penetration thickness of the radiation.

22. A computer-readable medium which stores a computer program for causing a computer to execute the step of;
reading an output value of a sensor in which a projection data of an object is generated:
calculating a penetration thickness of a radiation penetrated through the object by using a three-dimensional reconstruction image data reconstructed in accordance with a projection data of the object: and
calculating a calibration amount for calibrating an absorption coefficient of the radiation in the object by using a correspondence between the output value of the sensor and the penetration thickness of the radiation.

* * * * *

UNITED STATES PATENT AND TRADEMARK OFFICE
CERTIFICATE OF CORRECTION

PATENT NO. : 7,238,947 B2
APPLICATION NO. : 11/217609
DATED : July 3, 2007
INVENTOR(S) : Hiroyuki Oumi et al.

It is certified that error appears in the above-identified patent and that said Letters Patent is hereby corrected as shown below:

COLUMN 1:

Line 23, "coefficient u" should read --coefficient µ--;
Line 39, "p" should read --µ--; and
Line 41, "coefficient p" should read --coefficient µ--.

COLUMN 2:

Line 1, "No. H03-026241)" should read --(No. H03-026241).--.

COLUMN 4:

Line 38, "21B;" should read --21B,--.

COLUMN 9:

Lines 64-5, italics should be deleted.

COLUMN 13:

Line 12, "FIGS. 18A, 18C, 18C" should read --FIGS. 18A, 18B, 18C,--.

COLUMN 15:

Line 40, "attains" should read --attain--; and
Line 41, "themselves" should read --itself--.

COLUMN 16:

Line 15, "calibrate" should read --to calibrate--;

COLUMN 17:

Line 46, "farther" should read --further--.

UNITED STATES PATENT AND TRADEMARK OFFICE
CERTIFICATE OF CORRECTION

PATENT NO. : 7,238,947 B2
APPLICATION NO. : 11/217609
DATED : July 3, 2007
INVENTOR(S) : Hiroyuki Oumi et al.

It is certified that error appears in the above-identified patent and that said Letters Patent is hereby corrected as shown below:

COLUMN 18:

Line 20, "said" should read --wherein said--; and
Line 49, "step" should read --steps--.

Signed and Sealed this

Twenty Second Day of April, 2008

JON W. DUDAS
*Director of the United States Patent and Trademark Office*